(12) United States Patent
    Chen et al.

(10) Patent No.: US 9,236,633 B2
(45) Date of Patent: Jan. 12, 2016

(54) SYNTHESIS AND APPLICATIONS OF GRAPHENE BASED NANOMATERIALS

(71) Applicant: UWM Research Foundation, Inc., Milwaukee, WI (US)

(72) Inventors: Junhong Chen, Shorewood, WI (US); Marija Gajdardziska-Josifovska, Fox Point, WI (US); Carol Hirschmugl, Shorewood, WI (US); Eric Mattson, Kenosha, WI (US); Haihui Pu, Milwaukee, WI (US); Michael Weinert, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 276 days.

(21) Appl. No.: 13/916,033

(22) Filed: Jun. 12, 2013

(65) Prior Publication Data
US 2013/0344390 A1    Dec. 26, 2013

Related U.S. Application Data

(60) Provisional application No. 61/658,805, filed on Jun. 12, 2012, provisional application No. 61/717,849, filed on Oct. 24, 2012.

(51) Int. Cl.
*H01M 10/0525* (2010.01)
*C01B 31/04* (2006.01)
(Continued)

(52) U.S. Cl.
CPC ......... *H01M 10/0525* (2013.01); *C01B 31/043* (2013.01); *C30B 7/00* (2013.01); *C30B 19/00* (2013.01); *C30B 29/02* (2013.01); *C30B 29/60* (2013.01); *G01N 27/00* (2013.01);
(Continued)

(58) Field of Classification Search
CPC ............ B05D 3/10; B32B 9/00; C01B 31/02; C01B 31/00; B82Y 30/00
See application file for complete search history.

(56) References Cited

U.S. PATENT DOCUMENTS

| 7,658,901 B2 | 2/2010 | Prud'Homme et al. |
| 2010/0266964 A1 | 10/2010 | Gilje |

(Continued)

OTHER PUBLICATIONS

Mattson et al; Evidence of nanocrystalline semiconducting graphene monoxide during thermal reduction of graphene oxide in vacuum; ACS Nano (2011), 5(12), 9710-9717.*

(Continued)

*Primary Examiner* — Muhammad Siddiquee
(74) *Attorney, Agent, or Firm* — Michael Best & Friedrich LLP

(57) ABSTRACT

A composition of graphene-based nanomaterials and a method of preparing the composition are provided. A carbon-based precursor is dissolved in water to form a precursor suspension. The precursor suspension is placed onto a substrate, thereby forming a precursor assembly. The precursor assembly is annealed, thereby forming the graphene-based nanomaterials. The graphene-based nanomaterials are crystallographically ordered at least in part and configured to form a plurality of diffraction rings when probed by an incident electron beam. In one aspect, the graphene-based nanomaterials are semiconducting. In one aspect, a method of engineering an energy bandgap of graphene monoxide generally includes providing at least one atomic layer of graphene monoxide having a first energy bandgap, and applying a substantially planar strain is applied to the graphene monoxide, thereby tuning the first energy band gap to a second energy bandgap.

7 Claims, 25 Drawing Sheets

(51) Int. Cl.
| | |
|---|---|
| C30B 19/00 | (2006.01) |
| H01M 4/583 | (2010.01) |
| G01N 27/00 | (2006.01) |
| C30B 7/00 | (2006.01) |
| C30B 29/02 | (2006.01) |
| C30B 29/60 | (2006.01) |
| B82Y 40/00 | (2011.01) |
| G01N 27/12 | (2006.01) |
| B82Y 30/00 | (2011.01) |

(52) U.S. Cl.
CPC ............... *H01M 4/583* (2013.01); *B82Y 30/00* (2013.01); *B82Y 40/00* (2013.01); *G01N 27/127* (2013.01); *Y02E 60/122* (2013.01); *Y10S 977/734* (2013.01); *Y10S 977/892* (2013.01); *Y10S 977/932* (2013.01); *Y10S 977/948* (2013.01); *Y10S 977/957* (2013.01)

(56) References Cited

U.S. PATENT DOCUMENTS

| | | |
|---|---|---|
| 2011/0052813 A1 | 3/2011 | Ho et al. |
| 2011/0068290 A1 | 3/2011 | Haddon et al. |
| 2011/0189452 A1 | 8/2011 | Lettow et al. |

OTHER PUBLICATIONS

Acik, M. et al, The Role of Intercalated Water in Multilayered Graphene Oxide. ACS Nano, 2010, 5861-5868, 4(10).
Acik, M. et al, Unusual infrared-absorption mechanism in thermally reduced graphene oxide, Nature Materials, 2010, 840-845, 9(10).
Allred, A.L., Electronegativity values from thermochemical data, Journal of Inorganic and Nuclear Chemistry, 1961, 215-221, 17.
Bae, S. et al, Roll-to-roll production of 30-inch graphene films for transparent electrodes, Nature Nanotechnology, 2010, 574-578, 5(8).
Bagri, A. et al, Structural evolution during the reduction of chemically derived graphene oxide, Nature Chemistry, 2010, 581-587, 2(7).
Balandin, A.A. et al, Superior Thermal Conductivity of Single-Layer Graphene, Nano Letters, 2008, 902-907, 8(3).
Bao, W. et al, Controlled ripple texturing of suspended graphene and ultrathin graphite membranes, Nature Nanotechnology, 2009, 562-566, 4(9).
Beenakker, C.W.J. et al, Colloquium: Adreev reflection and Klein tunneling in graphene, Review of Modern Physiscs, 2008, 1337-1354, 80(4).
Berger, C. et al, Ultrathin Epitaxial Graphite: 2D Electron Gas Properties and a Route toward Graphene-based Nanoelectronics, J. Phys. Chem. B, 2004, 19912-19916, 108(52).
Bolotin, K.I. et al, Observation of the fractional quantum Hall effect in graphene, Nature, 2009, 196-199, 462(7270).
Bolotin, K.I. et al, Temperature-Dependent Transport in Suspended Graphene , Physical Review Letters, 2008, 096802, 101(9).
Bolotin, K.I. et al, Ultrahigh electron mobility in suspended graphene, Solid State Communications, 2008, 351-355, 146(9&10).
Boukhvalov, D.W. et al, Modeling of Graphite Oxide, Journal of American Chemistry Society, 2008, 10697-10701, 130(32).
Boykin, T.B. et al, Valence band effective-mass expressions in the sp(3)d(5)s(*) empirical tight-binding model applied to a Si and Ge parametrization, Phyiscal Review, 2004, 115201, 69(11).
Cai, W. et al, Thermal Transport in Suspended and Supported Monolayer Graphene Grown by Chemical Water Vapor Desposition, Nano Letters, 2010, 1645-1651, 10(5).
Campos, L.C. et al, Anistropic Etching and Nanoribbon Formation in Single-Layer Graphene, Nano Letters, 2009, 2600-2604, 9(7).
Cassagneau, T. et al, Preparation and Characterization of Ultrathin Films Layer-by-Layer Self-Assembled from Graphite Oxide Nanoplatelets and Polymers, Langmuir, 2000, 7318-7324, 16(18).
Dikin, D.A. et al, Preparation and characterization of graphene oxide paper, Nature, 2007, 457-460, 448(7152).

Dreyer, D.R. et al, From Conception to Realization: An Historical Account of Graphene and Some Perspectives for Its Future, Angew Chem., 2010, 9336-9345, 49.
Dreyer, D.R. et al, The chemistry of graphene oxide, Chemistry Society Review, 2010, 228-240, 39.
Eda, G. et al, Large-area ultrathin films of reduced graphene oxide as a transparent and flexible electronic material, Nature Nanotechnology, 2008, 270-274, 3(5).
Ekiz, O.O. et al, Reversible Electrical Reduction and Oxidation of Graphene Oxide, ACS Nano, 2011, 2475-2482, 5(4).
Erickson, K. et al, Determination of the Local Chemical Structure of Grapphene Oxide and Reduced Graphene Oxide, Advanced Materials, 2010, 4467-4472, 22(40).
Fano, U., Effects of Configuration Interaction on Intensities and Phase Shifts, Physical Review, 1961, 1866-1878, 124(6).
Fu, L.J. et al, Surface modifications of electrode materials for lithium ion batteries, Solid State Sciences, 2006, 113-128, 8.
Gao, W. et al, New Insights into the structure and reduction of graphite oxide, Nature Chemistry, 2009, 403-408, 1(5).
Giannozzi, P. et al, Quantum Espresso: a modular and open-source software project for quantum simulations of materials, Journal of Physics: Condensed Matter, 2009, 1-19, 21.
Gomez-Navarro, C. et al, Atomic Structure of Reduced Graphene Oxide, Nano Letters, 2010, 1144-1148, 10(4).
Han, M.Y. et al, Energy Band-Gap Engineering of Graphene Nanoribbons, Physical Review Letters, 2007, 206805, 98(20).
Hod, O. et al, Electromechanical Properties of Suspended Graphene Nanoribbons, Nano Letters, 2009, 2619-2622, 9(7).
Jang, S. et al, Flexible, transparent single-walled carbon nanotube transistors with graphene electrodes, Nanotechnology, 2010, 1-5, 21(42).
Joung, D. et al, High yield fabrication of chemically reduced graphene oxide field effect transistors by dielectrophoresis, Nanotechnology, 2010, 1-5, 21(16).
Ju, Y. et al, Microscopic four-point atomic force microscope probe technique for local electrical conductivity measurement, Review of Scientific Instruments, 2005, 086101, 76(8).
Jung, I. et al, Effect of Water Vapor on Electrical Properties of Individual Reduced Graphene Oxide Sheets, Journal of Physical Chemistry C, 2008, 20264-20268, 112(51).
Kim, K.S. et al, Large-scale pattern growth of graphene films for stretchable transparent electrodes, Nature, 2009, 706-710, 457(7230).
Kosynkin, D.V. et al, Longitudinal unzipping of carbon nanotubes to form graphene nanoribbons, Nature, 2009, 872-876, 458(7240).
Kuzmenko, A.B. et al, Determination of the gate-tunable band gap and tight-binding parameters in bilayer graphene using infrared spectroscopy, Physical Review Letters, 2009, 165406, 80(16).
Kuzmenko, A.B. et al, Gate Tunable Infrared Phonon Anomalies in Bilayer Graphene, Physical Review Letters, 2009, 116804, 103(11).
Kuzmenko, A.B. et al, Universal Optical Conductance of Graphite, Physical Review Letters, 2008, 117401, 100(11).
Lee, C. et al, Measurement of the Elastic Properties and Intrinsic Strength of Monolayer Graphene, Science, 2008, 385-388, 321(5887).
Lee, C.G. et al, Integration of reduced graphene oxide into organic field-effect transistors as conducting electrodes and as a metal modification layer, Applied Physics Letters, 2009, 023304, 95(2).
Li, D. et al, Graphene-Based Materials, Science, 2008, 1170-1171, 320(5880).
Li, D. et al, Processable aqueous dispersions of graphene nanosheets, Nature Nanotechnology, 2008, 101-105, 3(2).
Li, J. et al, Oxygen Driven Unzipping of Graphitic Materials, Physical Review Letters, 2006, 176101, 96(17).
Li, X. et al, Large-Area Synthesis of High-Quality and Uniform Graphene Films on Copper Foils, Science, 2009, 1312-1314, 324(5932).
Li, Z.Q. et al, Dirac charge dynamics in graphene by infrared spectroscopy, Nature Physics, 2008, 532-535, 4(7).
Liang, X. et al, Formation of Bandgap and Subbands in Graphene Nanomeshes with Sub-10 nm Ribbon Width Fabricated via Nanoimprint Lithography, Nano Letters, 2010, 2454-2460, 10(7).

(56) References Cited

OTHER PUBLICATIONS

Liao, L. et al, High-speed graphene transistors with a self-aligned nanowire gate, Nature, 2010, 305-308, 467(7313).
Liu, F. et al, Ab initio calculation of ideal strength and phonon instability of graphene under tension, Physical Review B, 2007, 064120, 76(6).
Lopez, V. et al, Chemical Vapor Deposition Repair of Graphene Oxide: A Route to Highly Conductive Graphene Monolayers, Advanced Materials, 2009, 4683-4686, 21(46).
Lu, G.H. et al, Gas Sensors Based on Tin Oxide Nanoparticles Synthesized from a Mini-Arc Plasma Source, Journal of Nanomaterials, 2006, 1-7, 60828.
Lu, G.H. et al, Reduced graphene oxide for room-temperature gas sensors, Nanotechnology, 2009, 1-9, 20(44).
Lu, G.H. et al, Toward Practical Gas Sensing with Highly Reduced Graphene Oxide: A New Signal Processing Method to Circumvent Run-to-Run and Device-to-Device Variations, ACS Nano, 2011, 1154-1164, 5(2).
Lu, Y. et al, High-On/Off Ratio Graphene Nanoconstriction Field-Effect Transistor, Small, 2010, 2748-2754, 6(23).
Mao, S. et al, A new reducing agent to prepare single-layer, high-quality reduced graphene oxide for device applications, Nanoscale, 2011, 2849-2853, 3.
Mao, S. et al, Graphene oxide and its reduction: modeling and experimental progress, RSC Advances, 2012, 2643-2662, 2.
Mao, S. et al, Specific Protein Detection Using Thermally Reduced Graphene Oxide Sheet Decorated with Gold Nanoparticle-Antibody Conjugates, Advanced Materials, 2010, 3521-3526, 22.
Mattson, E.C. et al, Evidence of Nanocrystalline Semiconducting Graphene Monoxide during Thermal Reduction of Graphene Oxide in Vacuum, ACS Nano, 2011, 9710-9717, 5(12).
Mattson, E.C. et al, Structure of Graphene Oxide-Tin Oxide Hybrid Nanomaterials for Gas Sensors, Microscopy and Microanalysis, 2010, 1708-1709, 16-2.
Meyer, J.C. et al, On the roughness of single- and bi-layer graphene membranes, Solid State Communications, 2007, 101-109, 143(1-2).
Mkhoyan, K.A. et al, Atomic and Electronic Structure of Graphene-Oxide, Nano Letters, 2009, 1058-1063, 9(3).
Mounet, N. et al, First-principles determination of the structural, vibrational and thermodynamic properties of diamond, graphite, and derivatives, Physical Review B, 2005, 205214, 71(20).
Nasse, M.J. et al, High-resolution Fourier-transform infrared chemical imaging with multiple synchrotron beams, Nature Methods, 2011, 413-416, 8(5).
Novoselov, K.S. et al, Electric Field Effect in Atomically Thin Carbon Films, Science, 2004, 666-669, 306(5696).
Novoselov, K.S. et al, Two-dimensional gas of massless Dirac fermions in graphene, Nature, 2005, 197-200, 438(7065).
Oostinga, J.B. et al, Gate-induced insulating state in bilayer graphene devices, Nature Materials, 2007, 151-157, 7.
Park, S. et al, Aqueous Suspension and Characterization of Chemically Modified Graphene Sheets, Chemistry of Materials, 2008, 6592-6594, 20(21).
Park, S. et al, Colloidal Suspensions of Highly Reduced Graphene Oxide in a Wide Variety of Organic Solvents, Nano Letters, 2009, 1593-1597, 9(4).
Perdew, J.P. et al, Generalized Gradient Approximation Made Simple, Physical Review Letters, 1996, 3865-3868, 77(18).
Pereira, V.M. et al, Tight-binding approach to uniaxial strain in graphene, Physical Review B, 2009, 045401, 80(4).
Poetschke, M. et al, Modeling graphene-based nanoelectromechanical devices, Physical Review B, 2010, 193404, 81(19).
Ponomarenko, L.A. et al, Chaotic Dirac Billiard in Graphene Quantum Dots, Science, 2008, 356-358, 320(5874).
Qi, Y. et al, Epitaxial graphene on SiC(0001): More than Just Honeycombs, Physical Review Letters, 2010, 085502, 105(8).
Rafiq, M.A. et al, High On/Off ratio and multimode transport in silicon nanochains field effect transistors, Applied Physics Letters, 2012, 113108, 100.
Sano, E. et al, Theoretical evaluation of channel structure in graphene field-effect transistors, Japanese Journal of Applied Physics, 2009, 041202, 48(4).
Seol, J.H. et al, Two-Dimensional Phonon Transport in Supported Graphene, Science, 2010, 213-216, 328(5975).
Son, Y.W. et al, Energy Gaps in Graphene Nanoribbons, Physical Review Letters, 2006, 216803, 97(21).
Stadelmann, P.A. et al, EMS—a Software Package for Electron Diffraction Analysis and HREM Image Simulation in Materials Science, Ultramicroscopy, 1987, 131-145, 21(2).
Stankovich, S. et al, Graphene-based composite materials, Nature, 2006, 282-286, 442(7100).
Stankovich, S. et al, Synthesis of graphene-based nanosheets via chemical reduction of exfoliated graphite oxide, Carbon, 2007, 1558-1565, 45(7).
Sun, J. et al, Controlling the Bonding and Band Gaps of Solid Carbon Monoxide with Pressures, Physical Review Letters, 2011, 1-4, 106(145502).
Szabo, T. et al, Evolution of Surface Functional Groups in a Series of Progressively Oxidized Graphite Oxides, Chemistry of Materials, 2006, 2740-2749, 18(11).
Tang, T. et al, A tunable phonon-exciton Fano system in bilayer graphene, Nature Nanotechnology, 2010, 32-36, 5.
Van Der Pauw, L.J., A Method of Measuring Specific Resistivity and Hall Effect of Discs of Arbitrary State, Philips Research Reports, 1958, 1-9, 13(1).
Wang, X. et al, Transparent, Conductive Graphene Electrodes for Dye-Sensitized Solar Cells, Nano Letters, 2008, 323-327, 8(1).
Wang, C. et al, Electrochemical Properties of Graphene Paper Electrodes Used in Lithium Batteries, Chemistry of Materials Communication, 2009, 2604-2606, 21.
Weinert, M. et al, FLAPW: applications and implementations, Journal of Physics: Condensed Matter, 2009, 084201, 21(8).
Wilson, N.R. et al, Graphene Oxide: Structural Analysis and Application as a Highly Transparent Support for Electron Microscopy, ACS Nano, 2009, 2547-2556, 3(9).
Xia, F. et al, Graphene Field-Effect Transistors with High On/Off Current Ratio and Large Transport Band Gap at Room Temperature, Nano Letters, 2010, 715-718, 10(2).
Xiang, H.J. et al, Structural motifs in oxidized graphene: a genetic algorithm study based on density functional theory, Physical Review B, 2010, 035416, 82(3).
Xiao, Z. et al, Field Electron Emission Characteristics and Physical Mechanism of Individual Single-Layer Graphene, ACS Nano, 2010, 6332-6336, 4(11).
Yang, D. et al, Chemical analysis of graphene oxide films after heat and chemical treatments by X-ray photoelectron and Micro-Raman spectroscopy, Carbon, 2009, 145-152, 47.
Yoo, E. et al, Large Reversible Li Storage of Graphene Nanosheet Families for Use in Rechargeable Lithium Ion Batteries, Nano Letters, 2008, 2277-2282, 8(8).
Zeinalipour-Yazdi, C.D. et al, Linear correlation between binding energy and Young's modulus in graphene nanoribbons, Journal of Applied Physics, 2009, 054318, 106(5).
Zhang, Y. et al, Direct observation of a widely tunable bandgap in bilayer graphene, Nature, 2009, 820-823, 459(7248).
Zhang, Y. et al, Experimental observation of the quantum Hall effect and Berry's phase in graphene, Nature, 2005, 201-204, 438(7065).
Zhou, S.Y. et al, Substrate-induced bandgap opening in epitaxial graphene, Nature Materials, 2007, 770-775, 6(10).
Zhu, Y. et al, Carbon-Based Supercapacitors Produced by Activation of Graphene, Science, 2011, 1537-1541, 332(6037).

\* cited by examiner

FIG. 6A
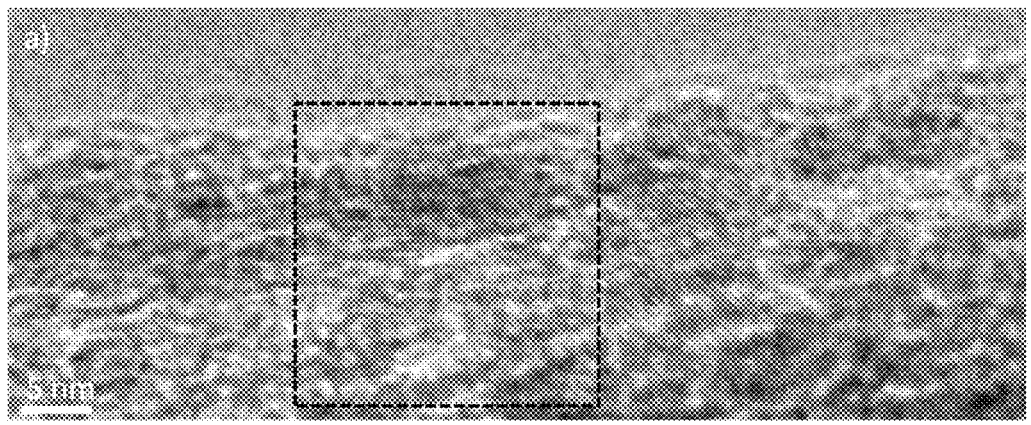
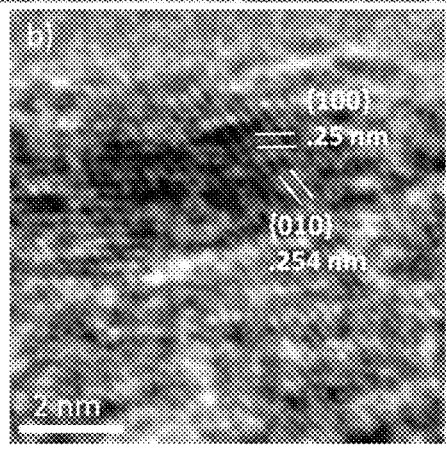
FIG. 6B
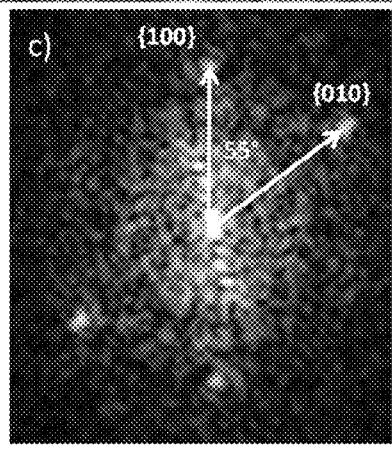
FIG. 6C

FIG. 8A
FIG. 8B
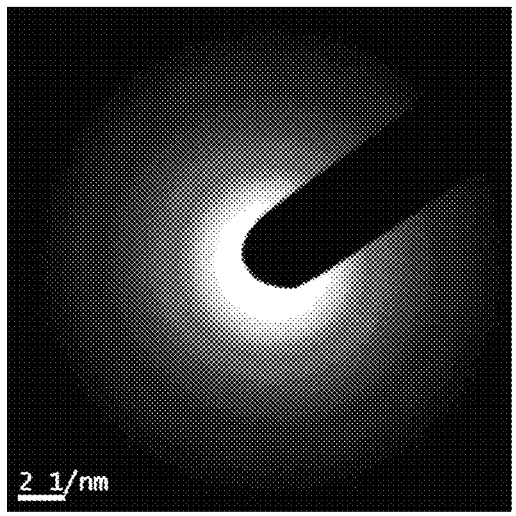
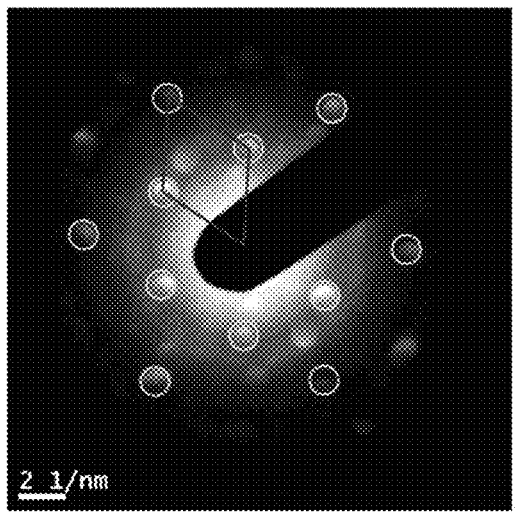

FIG. 9A   FIG. 9B
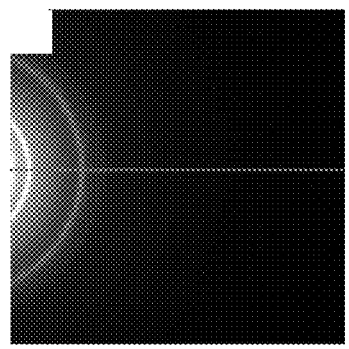
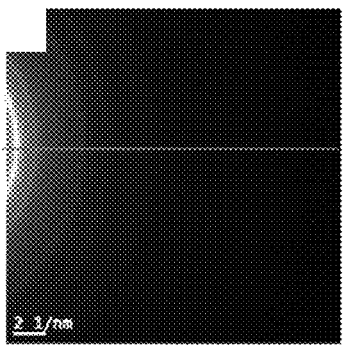
FIG. 9C
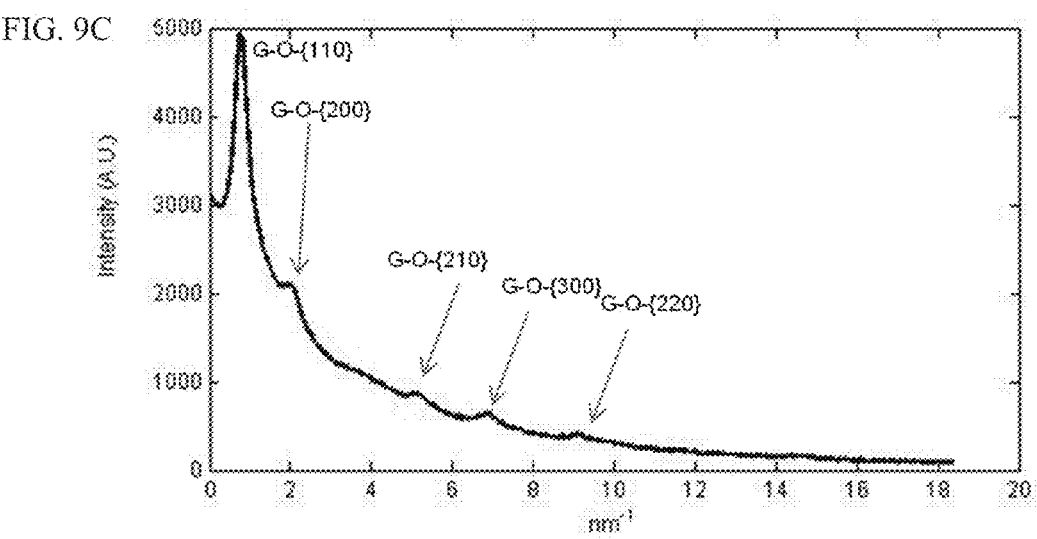
FIG. 9D
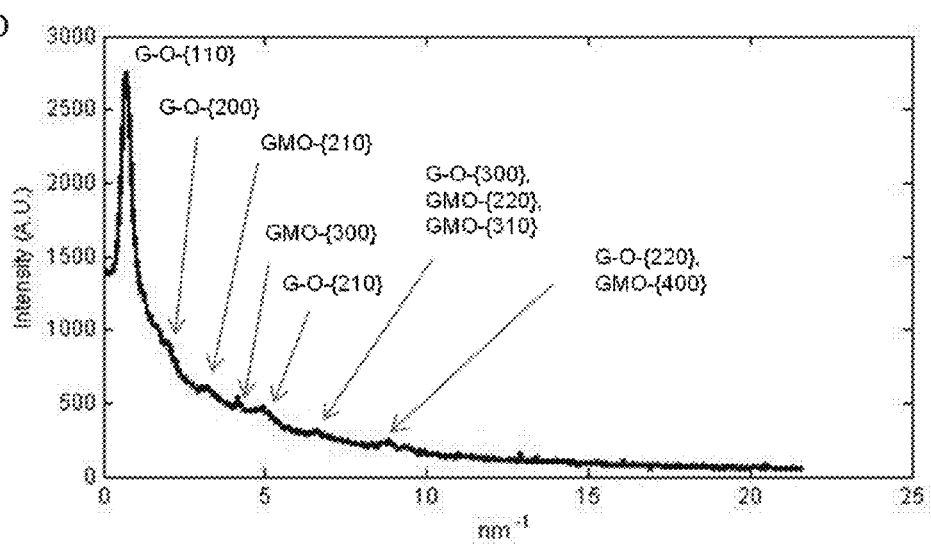

FIG. 11A
FIG. 11B
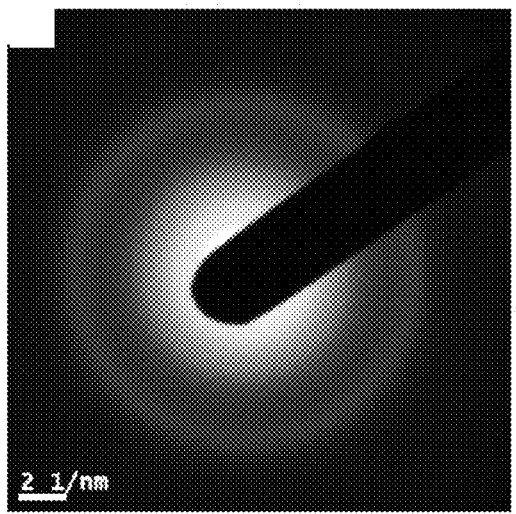
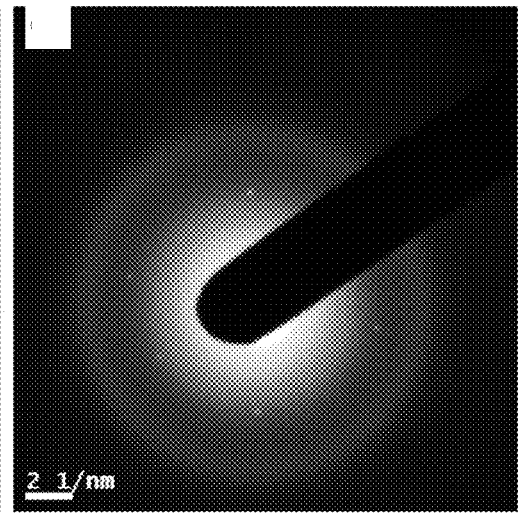

FIG. 14A
FIG. 14B
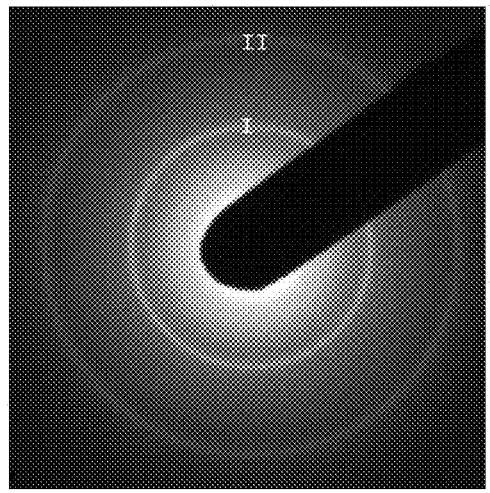
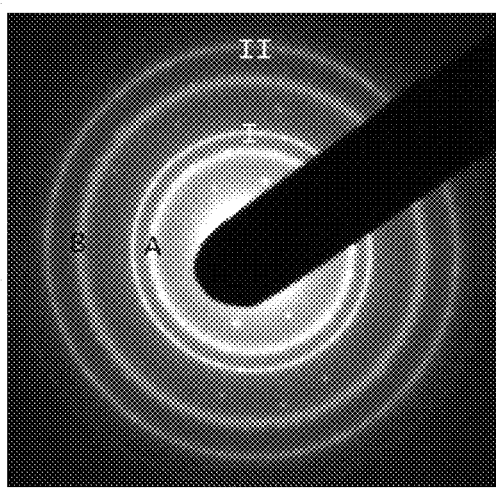

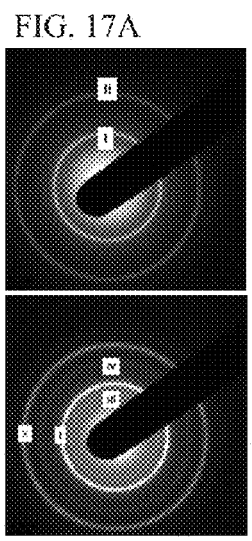 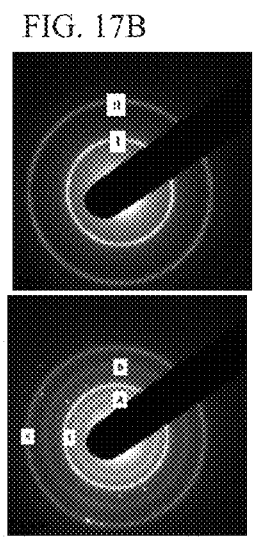 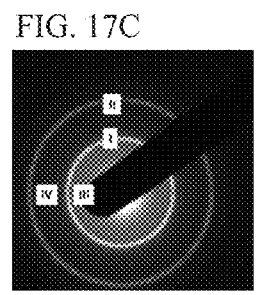 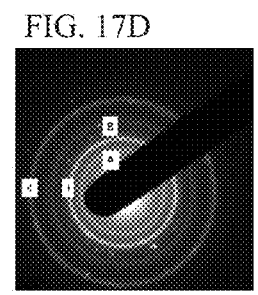
FIG. 17A  FIG. 17B  FIG. 17C  FIG. 17D
 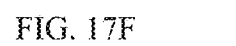
FIG. 17E  FIG. 17F FIG. 22A
FIG. 22B
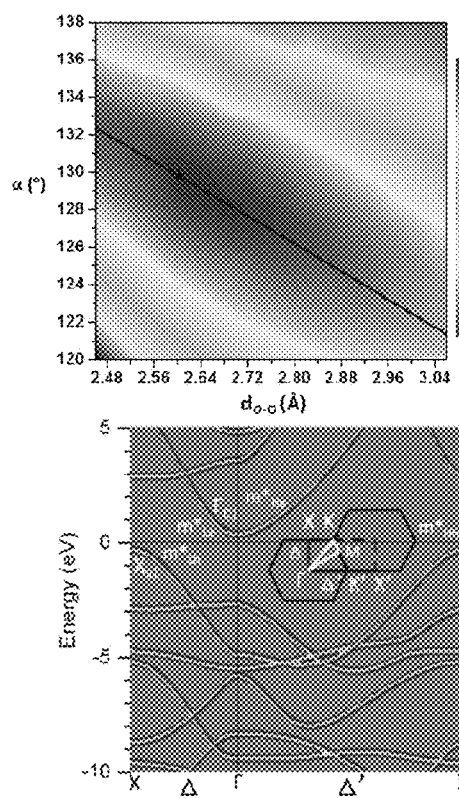
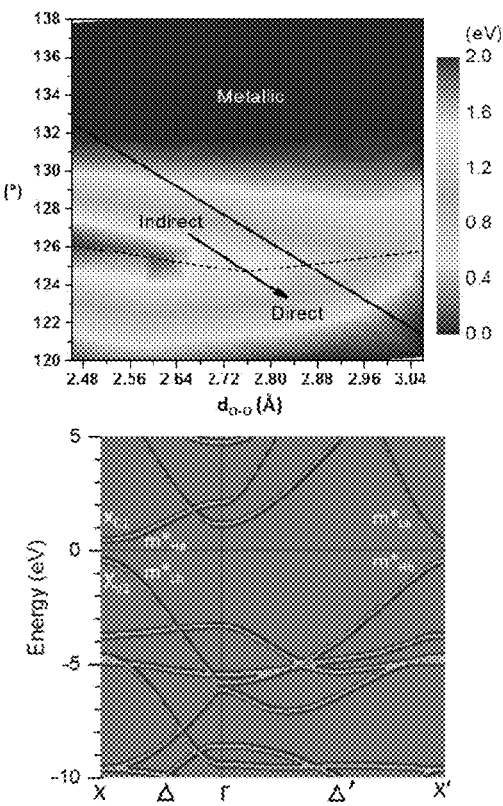
FIG. 22C
FIG. 22D FIG. 25A
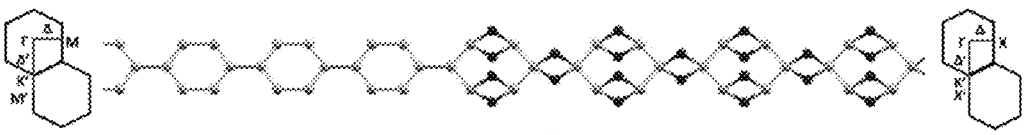
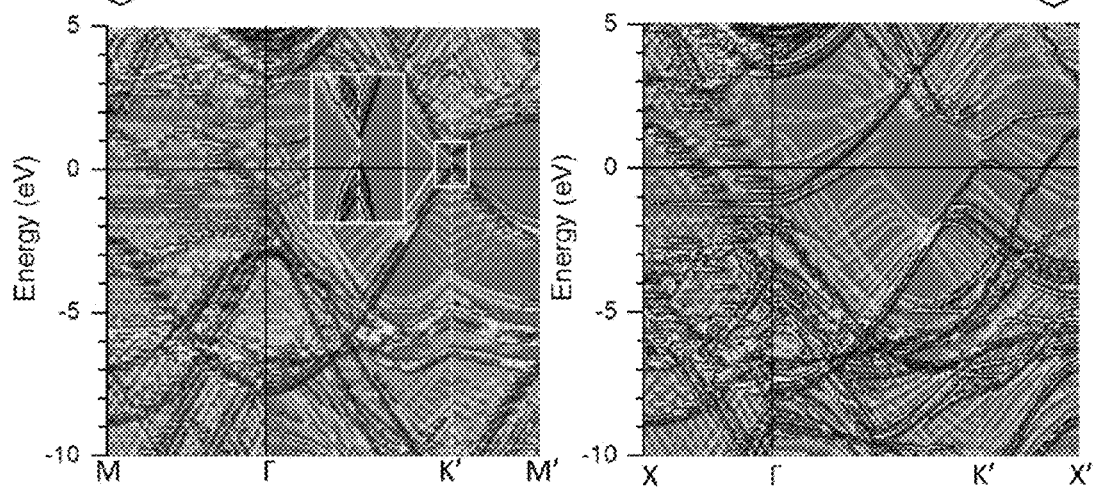
FIG. 25B FIG. 25C

US 9,236,633 B2

SYNTHESIS AND APPLICATIONS OF GRAPHENE BASED NANOMATERIALS

CROSS-REFERENCE TO RELATED APPLICATIONS

This application claims the benefit of U.S. Provisional Application No. 61/658,805, filed Jun. 12, 2012, and U.S. Provisional Application No. 61/717,849, filed Oct. 24, 2012, the entire contents of each which are hereby incorporated by reference.

STATEMENT REGARDING FEDERALLY SPONSORED RESEARCH

This invention was made with government support under grants DMR-0537588, DMR-0619759, CMMI-0856753, and CMMI-0900509, all awarded by the National Science Foundation (NSF). The government has certain rights in this invention.

BACKGROUND

Graphene is a single atomic layer of graphite. While the three dimensional crystal structure of graphite is hexagonal close packed, single graphitic layer or graphene has the structure of a hexagonal honeycomb. This structure of graphene can provide desirable properties, such as fractional quantum Hall effect, Andreev reflection and Klein tunneling, electron mobility up to about 200,000 $cm^2/Vs$ at room temperature, thermal conductivity ranging from about 3,000 $Wm^{-1}K^{-1}$ to about 5,000 $Wm^{-1}K^{-1}$ at room temperature, as well as high mechanical strength, e.g., a breaking strength of about 42 N/m. Because of these properties, graphene may be useful for electronic applications.

Known methods for production or synthesis of graphene include mechanical peeling or exfoliation of graphite crystals, and growth from vapor phase on epitaxially matched substrates, e.g., using chemical vapor deposition. However, the known methods are expensive and may not be suitable for scaling up.

SUMMARY

In one aspect, the invention provides a composition of graphene-based nanomaterials generally including at least one atomic layer of graphene monoxide. The graphene monoxide is crystallographically ordered at least in part and configured to form a plurality of diffraction rings when probed by an incident electron beam.

In another aspect, the invention provides a method of synthesizing graphene-based nanomaterials. A carbon-based precursor is dissolved in water to form a precursor suspension. The precursor suspension is placed onto a substrate, thereby forming a precursor assembly. The precursor assembly is annealed, thereby forming the graphene-based nanomaterials. In some aspects of the material formation the annealing can occur in wide range of vacuum or under partial pressures of water vapor.

In still another aspect, the invention provides a method of engineering an energy bandgap of graphene monoxide. At least one atomic layer of graphene monoxide having a first energy bandgap is provided. A substantially planar strain is applied to the graphene monoxide, thereby tuning the first energy band gap to a second energy bandgap. The nature of the first band gap is direct, and the second energy bandgap can be direct or indirect.

Other aspects of the invention will become apparent by consideration of the detailed description and accompanying drawings.

BRIEF DESCRIPTION OF THE DRAWINGS

FIGS. 6A and 6B are high-resolution transmission electron microscopy images of a thin region of a thermally reduced graphene oxide (TRG-O) film according to an embodiment of the present invention, and FIG. 6C is a diffractogram from the indicated region in FIG. 6A.

FIGS. 8A and 8B are in situ convergent beam electron diffracton (CBED) patterns for (a) unreduced GO observed before annealing and (b) the same material after annealing beyond 500° C., when GMO diffracting disks become visible (circled), according to embodiments of the present invention.

FIGS. 9A and 9B are selected area electron diffraction (SAED) patterns of (a) unreduced GO and (b) TRG-O according to embodiments of the present invention, and FIGS. 9C and 9D are line profiles taken from indicated regions of FIGS. 9A and, 9B, respectively with labeled diffraction peaks.

FIGS. 11A and 11B are in situ SAED patterns of (a) an unreduced GO monolayer collected at room temperature and (b) the monolayer after exceeding 800° C. according to embodiments of the present invention.

FIGS. 14A and 14B are SAED patterns of a GMO according to an embodiment of the present invention (a) before heating and (b) after exceeding 1200° C.

FIGS. 17A, 17B, 17C, 17D, 17E, and 17F are SAED patterns of a GMO according to an embodiment of the present invention (a) of a first region at 23° C., (b) of the first region at 620° C. after 19 minutes, (c) of the first region at 757° C. after 35 minutes, (d) of a second region at 756° C. after 40 minutes, (e) of a fourth region at 743° C. after 45 minutes, and (f) of a fifth region at 755° C. after 55 minutes.

FIG. 22A is a graph plotting distortion energies relative to a fully relaxed GMO structure per CO formula unit, FIG. 22B is a graph plotting a calculated band gap of a GMO according to an embodiment of the present invention as a function of lattice parameters, and FIGS. 22A and 22B are graphs plotting calculated bands of a GMO according to an embodiment of the present invention for $a_0=3.10$ Å and (a) $\alpha=130°$ C. and (b) $\alpha=125°$.

FIG. 25A is a schematic illustration of a GMO-graphene interface according to an embodiment of the present invention, and FIGS. 25B and 25C are graphs plotting projected band structures for graphene and GMO according to embodiments of the present invention.

DETAILED DESCRIPTION

Figure 1:
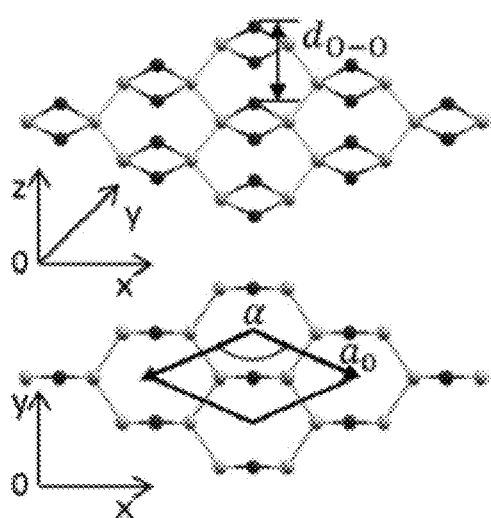
FIG. 1 is a schematic illustration of a graphene monoxide (GMO) according to an embodiment of the present invention.

Compositions of graphene-based nanomaterials generally including at least one atomic layer of graphene monoxide and methods of synthesizing the graphene-based nanomaterials are described herein. A carbon-based precursor is dissolved in water to form a precursor suspension. The precursor suspension is placed onto a substrate, thereby forming a precursor assembly. The precursor assembly is annealed, thereby forming the graphene-based nanomaterials. The graphene-based nanomaterials are crystallographically ordered at least in part and configured to form a plurality of diffraction rings when probed by an incident electron beam.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

Definitions

As used herein, "graphene monoxide" or "GMO" refers to a two-dimensional crystal graphene-based nanomaterial containing carbon and oxygen atoms in a 1:1 stoichiometry. GMO has a centered rectangular crystal structure, with each unit cell containing four oxygen (O) and four carbon (C) atoms. The same lattice can also be described with a quasi-hexagonal primitive cell with two 0 and two C atoms (FIG. 1). The bonding of each $C_2O_2$ unit is such that the atoms in a single unit cell form a double-epoxide ring. Each oxygen atom bridges two carbon atoms, forming a single bond with each of the two carbon atoms. Thus the carbon atoms in GMO form a single plane, and the oxygen atoms sit above and below the carbon plane.

Composition of Graphene-Based Nanomaterials

In one aspect, the invention features a composition of graphene-based nanomaterials generally including at least one atomic layer of GMO. The GMO is crystallographically ordered at least in part and configured to form a plurality of diffraction rings when probed by an incident electron beam. In some embodiments, the C—C bond lengths are from about 1.42 Å to about 1.60 Å. In certain embodiments, the C—O bond lengths are from about 1.34 Å to about 1.48 Å. Referring to FIG. 1 as an example, the C—C bonds in GMO can be 1.56

Å, and the C—O bond lengths can be 1.43 Å when the structure is relaxed. The dimensions of the unit cell and periodicity of the crystal lattice can be described by three geometrical values: the distance between nearest-neighbor oxygen atoms $d_{O-O}$, the primitive lattice constant $a_0$ and the opening angle α of the primitive unit cell. While the value of the primitive lattice constant $a_0$ is thermodynamically robust, a range of possible structures with varying $d_{O-O}$, and equivalent α are possible.

In some embodiments, the primitive lattice constant $a_0$ may be fixed within the range from about 0.305 nm to about 0.310 nm. This includes a primitive lattice constant $a_0$ of about 0.305 nm, about 0.306 nm, about 0.307 nm, about 0.308 nm, about 0.309 nm, or about 0.310 nm. In further embodiments, the opening angle α may range between from about 120° to about 130°. This includes an opening angle α of about 120°, about 121°, about 122°, about 123°, about 124°, about 125°, about 126°, about 127°, about 128°, about 129°, or about 130°. The range of structures encompassed by these parameters may be, given the substantial inhomogeneous broadening present in actual samples, generally within the experimental measurements of the periodicity of the GMO crystal structure.

In some embodiments, the composition may include at least one atomic layer of graphene. In further embodiments, the composition may include a nanocrystalline metal oxide, for example at least one of MoO, $MoO_2$, and $MoO_3$, or a nanocrystalline metal carbide such as $MoC_x$. In still further embodiments, the composition may include oxides or carbides of other transition metals, such as nickel, tungsten, niobium, hathium, scandium, titanium, vanadium, chromium, manganese, iron, cobalt, copper, zinc, yttrium, zirconium, and tantalum.

General Synthetic Description

In one aspect, GMO can be synthesized by dissolving a carbon-based precursor in water to form a precursor suspension. In certain embodiments, the carbon-based precursor is a solid, a liquid or a gas. In some embodiments, the carbon-based precursor includes at least one of graphite, graphene oxide, graphene, and carbon nanostructures such as nanotubes, nanorings, nanorods, and nanowires. One such carbon-based precursor, namely, graphene oxide, is available from ACS Material in Medford, Mass., and may be prepared using a modified Hummer's method. Carbon nanotubes are typically less than about 200 nm in diameter, and most typically less than 50 nm in diameter. Moreover, the nanotubes may be longer than about 500 nm, typically longer than about 2 μm, and most typically longer than about 5 μm. Nanorods and nanowires may have dimensions similar to those disclosed above for the nanotubes. In other embodiments, the carbon-based precursor may suitably include other materials.

In some embodiments, the precursor suspension has a concentration of the carbon-based precursor ranging from about 0.2 mg/ml to about 0.5 mg/ml. This includes a concentration of about 0.20 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.30 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.40 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, or about 0.50 mg/ml. In other embodiments, the precursor suspension may have any other suitable concentration of the carbon-based precursor.

The precursor suspension is placed onto a substrate, thereby forming a precursor assembly. In some embodiments, the precursor assembly comprises at least one transition metal. In some embodiments, the substrate comprises at least one transition metal. In further embodiments, the substrate is a perforated grid, such as a 200-mesh grid having 200 holes within 1 inch along a diameter direction. In other embodiments, the substrate may comprise other materials, e.g., oxides and carbides of transition metals, and/or may assume the form of a foil, wire, powder, or any other form suitable for placing the precursor suspension thereonto. In some embodiments, the substrate is immersed in the precursor suspension for a period of time from about 15 minutes to ten days or more. This includes immersing the substrate in the precursor suspension for about 11 days or more, about 12 days or more, about 13 days or more, about 14 days or more, about 15 days or more, about 16 days or more, about 17 days or more, about 18 days or more, about 19 days or more, about 20 days or more, about 21 days or more, about 22 days or more, about 23 days or more, about 24 days or more, about 25 days or more, about 26 days or more, about 27 days or more, about 28 days or more, about 29 days or more, about 30 days or more, about 31 days or more, or about 2 months or more. In some embodiments, the precursor suspension can be placed onto the substrate without immersing the substrate in the precursor suspension.

The precursor assembly is annealed, thereby forming the GMO. In some embodiments, the precursor assembly is annealed at a pressure of about $10^{-4}$ Pa or lower. This includes a pressure of about $9\times10^{-5}$ Pa or lower, about $8\times10^{-5}$ Pa or lower, about $7\times10^{-5}$ Pa or lower, about $6\times10^{-5}$ Pa or lower, about $5\times10^{-5}$ Pa or lower, about $4\times10^{-5}$ Pa or lower, about $3\times10^{-5}$ Pa or lower, about $2\times10^{-5}$ Pa or lower, about $1\times10^{-5}$ Pa or lower, about $9\times10^{-6}$ Pa or lower, of about $8\times10^{-6}$ Pa or lower, about $7\times10^{-6}$ or lower, about $6\times10^{-6}$ Pa or lower, about $5\times10^{-6}$ Pa or lower, about $4\times10^{-6}$ Pa or lower, about $3\times10^{-6}$ Pa or lower, about $2\times10^{6}$ Pa or lower, or about $1\times10^{-6}$ Pa or lower. In other embodiments, the precursor assembly may be annealed at a pressure ranging from about $1\times10^{-4}$ Pa to atmospheric pressure. In some embodiments, the precursor assembly is annealed at a temperature of about 500° C. or higher. This includes a temperature of about 500° C. or higher, about 600° C. or higher, about 700° C. or higher, about 800° C. or higher, about 900° C. or higher, about 1000° C. or higher, about 1100° C. or higher, or about 1200° C. or higher.

In certain embodiments, the carbon-based precursor is a solid which is added to a transition metal oxide or carbide suspension to form the precursor suspension.

Uses of the Graphene-Based Nanomaterials

As would be understood by one of ordinary skill in the art, the graphene-based nanomaterials according to the present invention may be used in many different end products. Because of its semiconducting properties, GMO may be useful for various electronic applications such as sensors, transistors, and optoelectronic devices, particularly considering its compatibility with graphene. For example, the graphene-based nanomaterials may be used as electrodes in a gas sensor or electrochemical cell such as lithium ion and lead acid batteries.

In some embodiments, a gas sensor may be constructed by affixing one or more electrodes to a substrate, wherein one or more electrodes are connected to a meter capable of measuring an electrical characteristic of the electrodes, or between the electrodes. The electrical characteristics detectable by the meter may include, but are not limited to, conductance, capacitance, potential, resistance, reluctance, inductance, magnetic field, and magnetic flux. Nanostructures may be deposited on the one or more electrodes, for example, by suspending nanostructures in a solvent solution and then evaporating the solvent to leave the nanostructures deposited upon the one or more electrodes. The graphene-based nanomaterials according to the present invention may then be deposited or decorated upon the nanostructures. Optionally, the nanostructures may be annealed before depositing the nanomaterials on the nanostructures. Depending upon the size and composition of the graphene-based nanomaterials, the gas sensor can be fabricated to be sensitive to a variety of gases, including toxic and flammable gases, which may include, but are not limited to $H_2$, $NO_2$, CO, $NH_3$, $H_2S$, and $CH_4$. Moreover, the gas sensor can have a substantially linear response over a desired concentration range.

Figure 2:
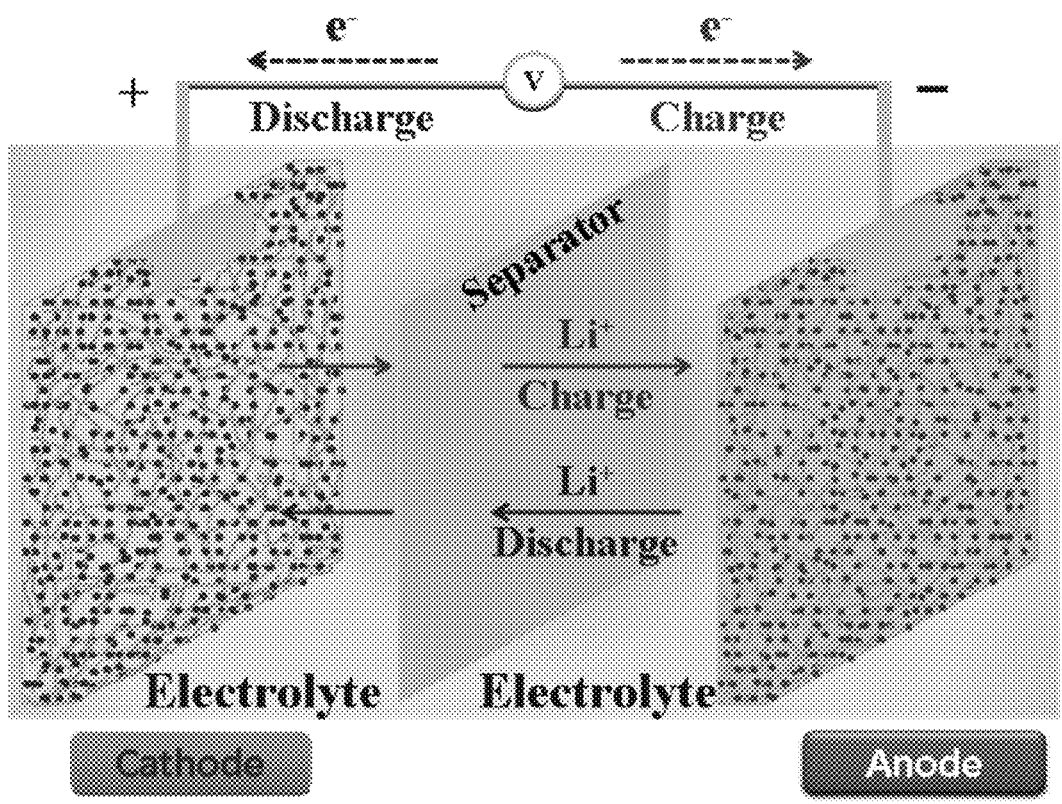
FIG. 2 is a schematic illustration of a lithium-ion battery including an anode with graphene-based nanomaterials prepared according to an embodiment of the present invention.

Lithium-ion batteries are single-use or rechargeable batteries that function by the discharge of positively charged lithium ions from an anode to a cathode through a separator. Lithium-ion batteries are typically capable of achieving a high energy density and a high cell voltage (e.g., 3.6 V), and may require low maintenance (low self-discharge and little periodic discharge needed). Referring to FIG. 2, a lithium-ion battery consists of three components: an anode, a cathode, and an electrolyte. For example, the electrolyte may include 1 M $LiPF_6$ in a mixture of ethylene carbonate (EC) and diethyl carbonate (DEC), with a volumetric proportion of EC:DEC=1:1. During discharge, lithium ions move from the anode to the cathode, producing current flow through the electrolyte solution.

In some embodiments of the present invention, graphene-based nanomaterials may be used as an anode material in single-use or rechargeable lithium-ion batteries. The graphene-based anode may possess unique electronic properties, such as an increased number of host sites available for lithium adsorbates, which may be important for single-use batteries. Furthermore, the graphene-based anode may possess attractive desorption characteristics, which may be important for rechargeable batteries. In addition, the graphene-based anode may have a high surface-area-to-volume ratio, which may improve gravimetric capacity of the anode compared to conventional anodes made of graphite. In addition, multilayers of the graphene-based materials may have attractive lithium intercalation and deintercalation properties.

In some embodiments, the graphene-based nanomaterials may be used as a support or scaffold for heterostructure nanomaterials or nanostructures, wherein the nanostructure is configured to support at least one of a metal or metal oxide atom, molecule, cluster, and nanocrystal. In other embodiments, the graphene-based nanomaterials may be used in other nanostructures.

Method of Engineering an Energy Bandgap of GMO

In one aspect, the invention provides a method of engineering an energy bandgap of GMO. Although graphene has been considered as a replacement for silicon in digital logic circuits due to its high electron transport properties, its semimetallic nature may limit its use in semiconductor applications. For example, known graphene-based transistors may achieve a cutoff frequency as high as 300 GHz, but the on/off ratio at room temperature may only be about 1,000, which is lower compared to that of silicon transistors (>10,000).

In some embodiments of the present invention, at least one atomic layer of free-standing GMO having a first energy bandgap is provided. A substantially planar strain is applied to the GMO, thereby tuning the first energy bandgap to a second energy bandgap. For example, the substantially planar strain may be applied by at least one of a mechanical stress, a piezoelectric mechanism, and a magnetoelectric mechanism.

In some embodiments, the second energy bandgap is from 0 eV to about 1.35 eV, and can be different from the first energy bandgap by more than about 1 eV. For example, the second energy bandgap may be different from the first energy bandgap by at least about 0.1 eV, at least about 0.2 eV, at least about 0.3 eV, at least about 0.4 eV, at least about 0.5 eV, at least about 0.6 eV, at least about 0.7 eV, at least about 0.8 eV, at least about 0.9 eV, or at least about 1.0 eV. In some embodiments, the GMO defines an opening angle and a rectangular cell length, and applying the substantially planar strain varies at least one of the opening angle and the rectangular cell length.

In some embodiments, the GMO includes carbon atoms in a zigzag arrangement defining a zigzag crystallographic direction, and the substantially planar strain is applied along the zigzag crystallographic direction. For example, the free-standing GMO may have a first opening angle of about 130 degrees and a first energy bandgap of about 0.61 eV. A substantially planar tensile strain may be applied along the zigzag crystallographic direction, whereupon the first opening angle is varied to a second opening angle of about 126 degrees, and the second energy bandgap reaches a maximum of about 1.35 eV. Upon further stretching along the zigzag crystallographic direction from the opening angle of about 126 degrees to about 121 degrees, the energy bandgap varies from a maximum of about 1.35 eV to about 0.1 eV.

In some embodiments, the GMO includes carbon atoms in an armchair arrangement defining a longitudinal crystallographic direction. For example, the GMO may include armchair graphene nanoribbons. The substantially planar strain may then be applied along the longitudinal crystallographic direction.

Method of Tuning a Thermal Conductivity of GMO

In one aspect, the invention provides a method of tuning a thermal conductivity of GMO. At least one atomic layer of free-standing GMO having a first thermal conductivity is provided. The GMO may include carbon atoms in an arrangement defining a zigzag crystallographic direction and a longitudinal crystallographic direction. In some embodiments, the first thermal conductivity may be about 600 $Wm^{-1}K^{-1}$ along the zigzag crystallographic direction, and about 3,000 $Wm^{-1}K^{-1}$ along the longitudinal crystallographic direction, both at room temperature. A substantially planar strain is applied to either the zigzag or longitudinal crystallographic direction, thereby tuning the first thermal conductivity to a second thermal conductivity. For example, the thermal conductivity can be increased by applying a tensile strain along the longitudinal crystallographic direction, and decreased by applying a tensile strain along the zigzag crystallographic direction. In some embodiments, the GMO can be placed onto a substrate having surface texture extending along the zigzag or longitudinal crystallographic direction, respectively, thereby decreasing the thermal conductivity along the respective direction.

The following Examples are intended to illustrate the invention above and should not be construed as to narrow its scope. One skilled in the art will readily recognize that the Examples may suggest other ways in which the present invention could be practiced. It should be understood that variations and modifications may be made while remaining within the scope of the invention.

EXAMPLES

Example 1

Thermal Reduction of Graphene Oxide in Vacuum

GO suspensions (referred to as "Austin sample") were synthesized using a modified Hummers method, as described in Sungjin Park, Jinho An, Richard D. Piner, Inhwa Jung, Dongxing Yang, Aruna Velamakanni, SonBinh T. Nguyen, and Rodney S. Ruoff, *Aqueous Suspension and Characterization of Chemically Modified Graphene Sheets*, 20 (21) CHEM. MATER. 6592 (2008) (hereby incorporated by reference). GO multilayer samples were prepared by drop-casting 2 µl of the resulting suspension onto bare 200 mesh Mo Transmission Electron Microscopy TEM grids. The starting Mo grid was studied by XPS and found to have predominant surface oxidation composition of $MoO_3$, with smaller presence of $MoO_2$. The individual GO monolayers became stacked after water evaporation, forming self-supporting multilayer structures that span the grid holes. Monolayer GO samples were prepared by drop-casting diluted suspensions into Si TEM grids with an ultrathin $Si_3N_4$ membrane.

TEM studies were performed in situ using a Gatan tantalum-cup heating holder inside a Hitachi H9000NAR TEM operating at an accelerating voltage of 300 keV. The column pressure of the TEM was maintained in the low $10^{-7}$ ton (equivalent to high $10^{-5}$ Pa). The TEM is equipped with a Gatan Orius SC CCD, which was used to record diffraction movies with 1 frame (1 s exposure time) per 4 seconds. A selected area electron diffraction (SAED) pattern of the GO film was recorded during the vacuum annealing process, allowing structure to be correlated with temperature that was detected with a thermocouple. SAED patterns were recorded both during and after annealing of the sample, indicating that the structural changes observed during the experiment were stable upon cooling the sample to room temperature. A radially averaged profile of diffraction intensity (such as displayed in the insets of FIG. 3(a)) was extracted from each frame of the SAED movie corresponding to the temperature of the sample, and subsequently combined as FIG. 3(b), thus indicating the evolution of the reciprocal space positions (y-axis) of the diffracted electrons with increasing temperature (x-axis). During annealing and after being cooled, the samples were studied using SAED, convergent beam electron diffraction (CBED), high-resolution transmission electron microscopy (HRTEM), and bright-field TEM. In other in situ experiments, a CBED pattern, taken with a 17 nm convergent beam electron probe, was examined as the samples were reduced.

After TEM analysis, Infrared Microspectroscopy (IRMS) was performed on the same TRG-O samples. IR measurements were performed at the Synchrotron Radiation Center (SRC, Stoughton, Wis.) at the IRENI beamline. The films as prepared on TEM grids were measured in a Bruker Hyperion 3000 IR Microscope coupled to a synchrotron source. Normal incidence transmittance and reflectance measurements were performed on the free standing films supported on TEM grids. By repeating the experiments with objectives of different numerical aperture, measurement effects resulting from convergence of the synchrotron beam being focused by the Schwarzschild focusing optics were ruled out. The films were subsequently removed from the grids and placed on microscope slides with an IR reflective coating (Kevely Technologies). This enabled the films to be measured at a grazing incidence using a Bruker Grazing Angle IR microscope objective lens. GI measurements were performed with an IR polarizer to emphasize only radiation polarized parallel to the plane of incidence.

Density functional calculations were carried out using the all-electron Full-potential Linearized Augmented Plane Wave method, as implemented in flair. The GMO and graphene calculations used the generalized gradient approximation (GGA) of Perdew, Burke, and Ernzerhof for exchange-correlation; sphere radii of 1.2 $a_B$ for both C and O; plane wave basis and charge/potential representation cutoffs of 275 and 2700 eV, respectively; 12×12×2 to 36×36×2 k-point sets; and vacuum regions of 15 Å. The internal coordinates were relaxed to a force criterion of 10-4 eV/Å. Other C:O ratios and configurations were modeled starting from 2×2 hexagonal cells with 8 carbon atoms.

Figure 3A:
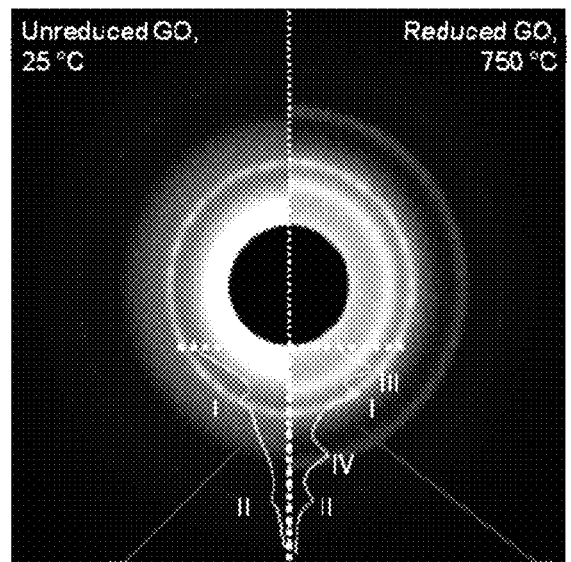
FIGS. 3A, 3B and 3C are a schematic illustration of an evolution of electron diffraction patterns with temperature of a graphene oxide (GO) sample according to an embodiment of the present invention. New diffraction rings, marked III and IV, denote the newly discovered grapheme monoxide (GMO) phase. Along with the graphene diffraction rings, I and II, and the changed background intensity, this new composite material is referred to as vacuum thermally reduced graphene oxide (VTR-GO, or reduced-GO).

Referring to FIG. 3(a), SAED patterns of a multilayer GO film before (left) in situ vacuum annealing are compared to those during (right) the in situ vacuum annealing at 750° C. Before annealing, the primary features evident in FIG. 3(a) are the diffraction rings (labeled as I and II) from spacings of 0.213 nm and 0.123 nm, respectively, corresponding to the {100}- and {110}-type reflections of graphene. A ring pattern is observed rather than a spot pattern due to the fact that the sample consisted of a large number of randomly oriented layers (see FIG. 8). Analysis of the relative intensities showed that the {100} type reflections produced a greater diffracted intensity than the {110} reflections, indicating that the layers were monolayers with disordered stacking, as opposed to few-layer Bernal-stacked graphite. Moreover, SAED patterns (FIG. 9) recorded at higher scattering angles (i.e., smaller lattice spacing), indicated weaker higher order rings consistent with crystalline graphene. In addition, SAED patterns recorded before annealing (FIG. 3(a), left) showed two broad amorphous rings centered at about 0.27 and 0.52 $Å^{-1}$ (0.370 nm and 0.185 nm in real space). Though not wishing to be bound by a particular theory, the amorphous rings are attributable to the first- and second-order reflections from nearest-neighbor disordered species.

Figure 3B:
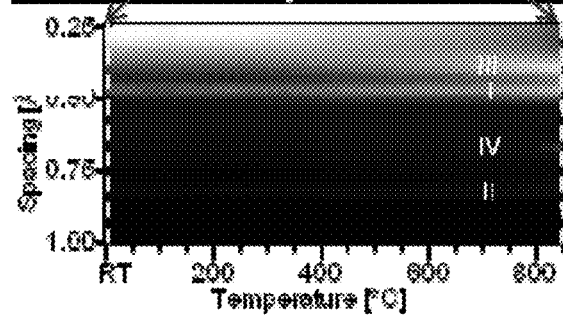

While annealing the multilayer GO film, two prominent new rings (labeled as III and IV) developed corresponding to spacings of about 0.260 nm and 0.152 nm, respectively, while the graphene rings (I and II) remained largely unchanged (FIG. 3(a)). Thus the SAED data demonstrated that a new crystalline phase developed upon annealing. A visualization of the complete temperature-dependent evolution of SAED patterns from the GO film annealing is shown in FIG. 3(b). Diffraction rings in a conventional SAED pattern (FIG. 3(a)) appeared as horizontal lines in the representation of FIG. 3(b). From FIG. 3(b), it is evident that the graphene rings, I and II, grew in intensity as the sample was annealed, but that they remained essentially fixed in reciprocal space position. The new crystalline GMO phase characterized by peaks III and IV, however, shows a qualitatively different behavior with temperature. The broad amorphous peak (associated with the disordered functional groups) initially centered at about 0.27 $Å^{-1}$ appears to split into two bands, one of which evolves in position and intensity into the crystalline reflection of the GMO phase labeled as III. The remaining amorphous contributions shift closer to the reciprocal space origin and show a reduction in intensity, evident in the 300° C.-500° C. temperature range, with similar behavior observed in band IV. This structural ordering did not produce visible features in bright field TEM images, indicating that the multilayer morphology was preserved and that the new phase had a 2D structure. The evolution of the SAED patterns was observed across the entire sample and was constant upon cooling the sample, thus ruling out effects related to sample drift. These observations were reproducible in numerous experiments.

Figure 3C:
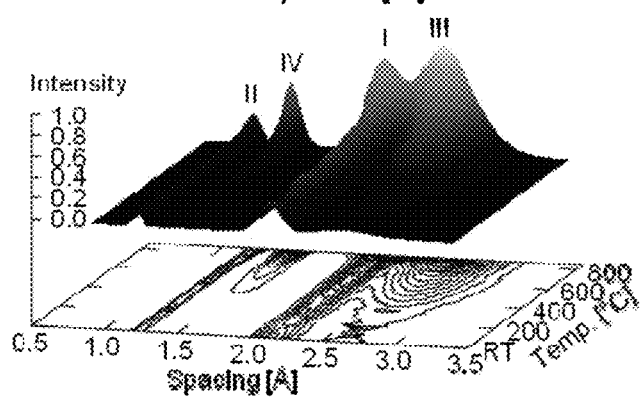
Figure 10:
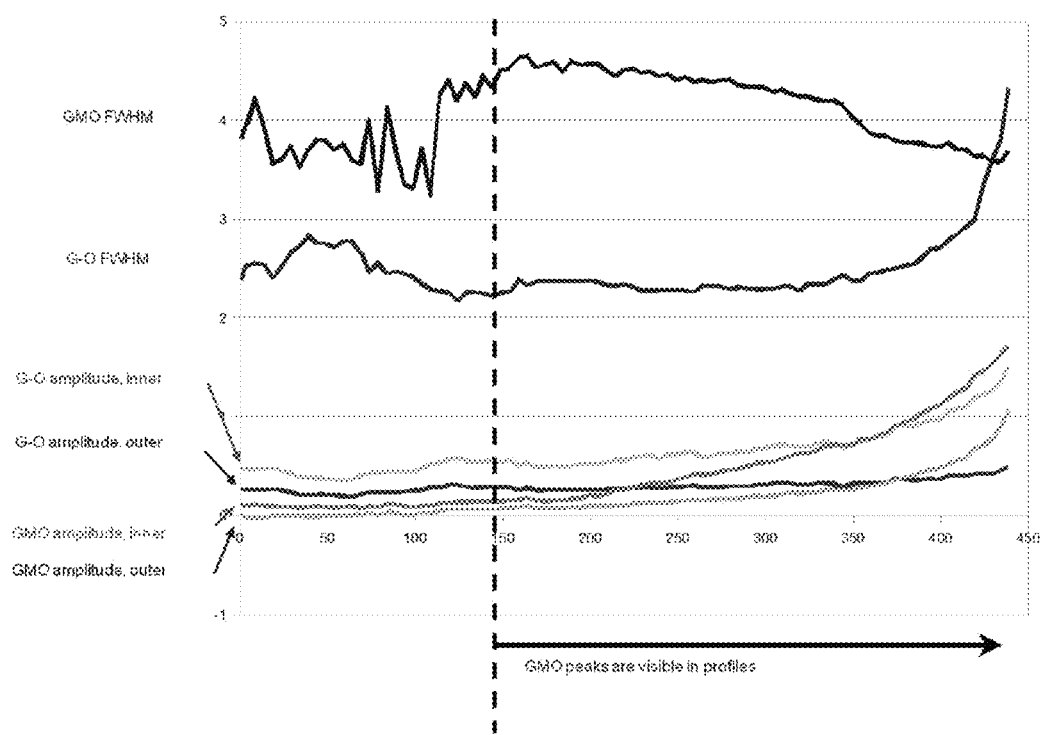
FIG. 10 is a graph plotting SAED temperature-dependent fitting parameters of GO/graphene and GMO diffraction peaks according to embodiments of the present invention. The horizontal axis denotes frame numbers in a digital movie that captures the creation of the new materials (to teright of the dashed vertical line). The vertical axis shows fitted amplitudes of the experimental diffraction peaks of G and GMO, and fitted widths as full width half maxima (FWHM) of the diffraction peaks.

To quantify the temperature evolution of the diffraction data, individual profiles of FIG. 3(b) over the complete temperature range were fit with a set of Gaussians (see FIG. 10). FIG. 3(c) shows the fitting results for the crystalline diffraction bands I-IV without the background and amorphous contribution where several key features of the structural evolution of the GO film are observed. First, the integrated intensity of the graphene peaks I and II, related to the volume fraction of scattering material, more than doubled. Similarly, the integrated intensity of peaks III and IV (GMO phase) grew rapidly from zero in the starting material to more than 1.5 times that of the graphene phase at the end of the annealing. These integrated intensities may be considered in terms of qualitative increases and decreases in quantity of material. Second, from the results shown in FIG. 3(c), the ratio of peak positions for the graphene phase (peaks I and II) maintained the value √3 (with absolute deviation due to thermal expansion less than 0.1%) for an ideal hexagonal structure. The thermal evolution of the GMO peaks III and IV, while nearly √3 in ratio, deviated 1-2% (depending on temperature) from the ideal hexagonal crystalline symmetry. Though not wishing to be bound by a particular theory, this deviation from hexagonal symmetry, too large to be associated with thermal expansion, indicates that the crystalline phase associated with the diffraction rings III and IV was centered rectangular, albeit nearly hexagonal (quasi-hexagonal), and distinct from the graphene phase characterized by diffraction rings I and II.

To elucidate the in situ SAED observations, the geometrical bonding of the films was investigated before and after annealing by IRMS. Using normal incidence (NI) transmission and grazing incidence (GI) reflectance, vibrational modes with dynamic dipole moments parallel or perpendicular to the basal plane of the films, respectively, were resolved. FIGS. 4(a)-4(d) show IR absorbance of the samples before and after annealing as measured in NI and GI. The features in the NI spectrum of GO (FIG. 4(a)) indicate the presence of oxygen functional groups including hydroxyl (3,300 $cm^{-1}$), carbonyl (1,708 $cm^{-1}$), carboxyl (1,425 $cm^{-1}$), epoxide (1,245 $cm^{-1}$, 900 $cm^{-1}$), and alkoxy (1,080 $cm^{-1}$). Though not wishing to be bound to a particular theory, the feature at 1,580 $cm^{-1}$ can be assigned to the C=C stretch of the underlying carbon lattice which is activated in GO due to oxygen functional groups and defects. The GI IR (FIG. 4(c)) absorbance spectrum of GO also indicated the presence of O—H from intercalated water (stretching modes at 3,300-3,600 $cm^{-1}$, bending mode at 1,645 $cm^{-1}$), as well as carbonyl (1,708 $cm^{-1}$) and hydroxyl (C—OH stretching at 1,070 $cm^{-1}$).

Figure 4A:
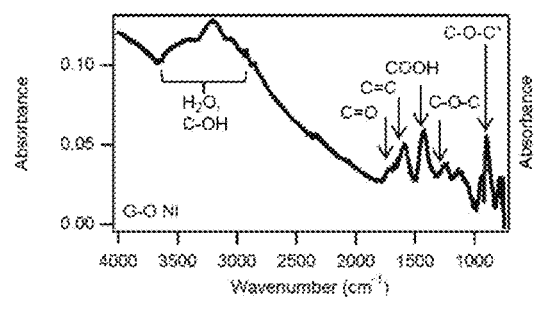
FIGS. 4A, 4B, and 4C, and 4D are graphs plotting normal incidence (NI) infrared absorbance spectra of (a) unreduced graphene oxide, (b) thermally reduced grapheme oxide (TRG-O), and grazing incidence (GI) infrared absorbance spectra of (c) GO, and (d) TRG-O, all according to embodiments of the present invention.
Figure 4B:
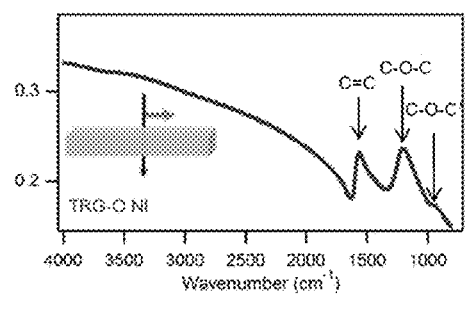
Figure 4C:
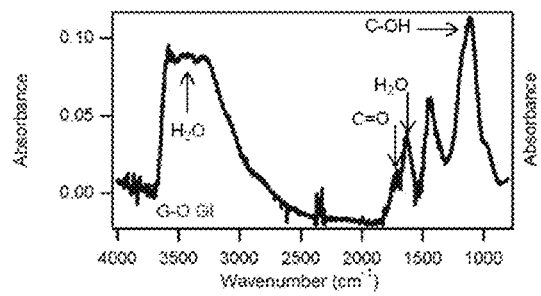
Figure 4D:
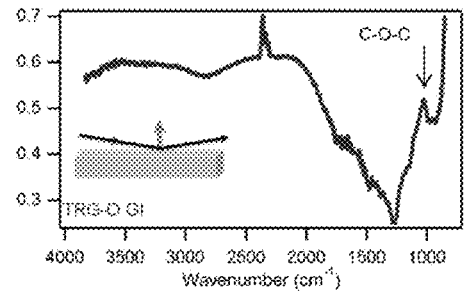

After annealing, many of the oxygen functionalities including carbonyl, carboxyl, alkoxy, and hydroxyl were no longer present in the NI IR spectrum of TRG-O (FIG. 4(b)). The C=C stretching mode softened in frequency and evolved into an asymmetric Fano lineshape, indicating a continuum of electronic transitions with symmetries parallel to the C=C vibrational excitation spanning at least 0.18-0.21 eV. The C=C stretching mode, which was inactive in pure graphene and graphite due to symmetry considerations, was activated due to defects and neighboring oxidized regions. The C—O—C asymmetric stretching mode, whose overall intensity increases dramatically, was softened by about 25 $cm^{-1}$. Analysis of this mode from the same position of the same sample before and after annealing showed that the integrated intensity of the C—O—C asymmetric stretching band increased by a factor of approximately 20 after the annealing process. The doublet assigned to C—O—C bending had diminished intensity and appeared as a single peak in the annealed spectrum. GI IR absorption spectra from samples after annealing are also shown in FIG. 4(d), where many oxygen features are missing, including notably, those associated with water. While the C—O—C mode at 1,205 $cm^{-1}$ is weakly active in this geometry, a prominent new mode is seen at 1,050 $cm^{-1}$. Thus, the nano-crystalline phase contained structures that gave rise to two distinct vibrational modes involving C—O displacements that were active in the NI geometry, and one C—O mode that was active in the GI geometry.

The electron diffraction data presented in FIG. 3 show that the vacuum thermal reduction of multilayered GO resulted in a two-phase nanoscale system containing regions of graphene and a crystalline phase. A C:O ratio of 2:1 was observed through XPS measurements, with slowly varying stoichiometry across the sample. From the IR results above, the new crystalline phase was determined to be an ordered solid-state carbon-oxide, with exactly three IR active normal modes of vibration involving C—O—C atomic displacements. High camera length diffraction patterns from the carbon-oxide phase, which probes reciprocal spacings closer to the origin, indicated that the 0.260 nm spacing is the lowest order reflection of the crystalline unit cell, corresponding to a unit cell about 20% larger than graphene. Therefore, the electron diffraction data indicated a quasi-hexagonal unit cell, which can also be described as centered rectangular.

Figure 5A:
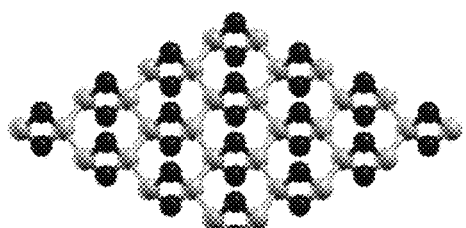
FIGS. 5A, 5B, and 5C are schematic illustrations of a GMO and its molecular vibration modes according to an embodiment of the present invention.
Figure 5B:
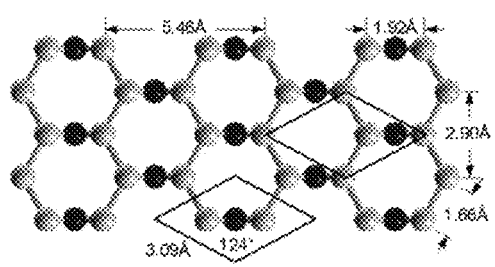
Figure 5C:
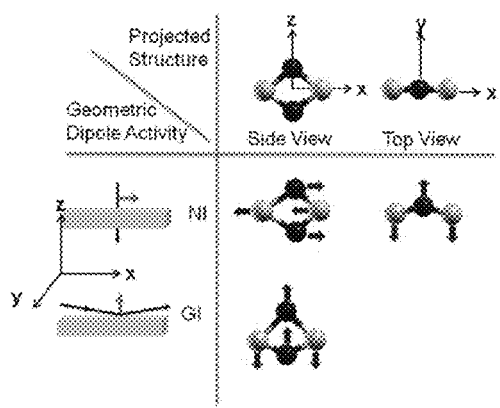

DFT calculations demonstrated that adding oxygen to graphene is energetically favorable, leading to the proposed quasi-hexagonal double-epoxide structure (FIG. 5(a)-5(b); C:O=1:1) with a binding energy of 4.36 eV/O. This is significantly higher than previously reported GO configurations with high epoxide coverage, where ordered epoxide groups in a $C_2O$ structure yielded a calculated binding energy of 3.73 eV/O. The calculated lattice parameters of this centered-rectangular (quasi-hexagonal) structure are given in FIG. 5(b). Compared with graphene, the magnitude of the primitive lattice vectors increased to 3.09 Å (from 2.46 Å) and the angle between them was 124° versus the 120° of an ideal hexagonal lattice. Although this structure no longer had the 3-fold symmetry of the graphene lattice, there were three sets of mirror planes, corresponding to $D_{2h}$ symmetry, which implies that there are three IR-active vibrational modes (FIG. 5(c)) two C—O—C modes in NI and one C—O—C mode in GI, as observed experimentally. The 0 to C ratio in the oxidized regions was significantly higher than previously reported values in unreduced multilayer GO where the average chemical compositions vary from $C_1O_{0.17}H_{0.08}$ to $C_1O_{0.49}H_{0.2}$ depending on the oxidation time and methods. Experimentally an increase was observed in diffracted intensity of the original GO/graphene reflections, which indicated a concurrent increase in the crystalline areas of graphene-like islands that are oxygen-free regions. Notably, the increase in stoichiometry was localized to small crystalline regions of GMO, and the overall oxygen content of the entire sample had not increased. Though not wishing to be bound by a particular theory, the formation of the new composite nano-material is likely a consequence of the large number of layers in the starting material and the diffusion-limited nature of the reduction process. When similar in situ vacuum annealing experiments were performed on a monolayer GO sample, the GMO phase was not observed (FIG. 11).

The atomic resolution HRTEM image in FIG. 6(a) shows that lattice fringes from individual GMO domains can be resolved in thin regions of the sample edges. FIG. 6(b) shows an enlargement of a single GMO domain from the HRTEM image in FIG. 6(a), with the numerical diffractogram from the same region shown in FIG. 6(c). In FIG. 6(b), high frequency components of the image beyond the lattice resolution of the microscope were filtered out. In the diffractogram of this region, two reflections were observed with measured spacings of 0.25 nm and 0.254 nm, corresponding to both the {100} and {010}-type reflections of GMO. Measurement of the angle between the sets of lattice fringes yielded an angle 55°. These results further confirmed the structural conclusions based on all SAED, IRMS, and DFT analyses.

Figure 7A:
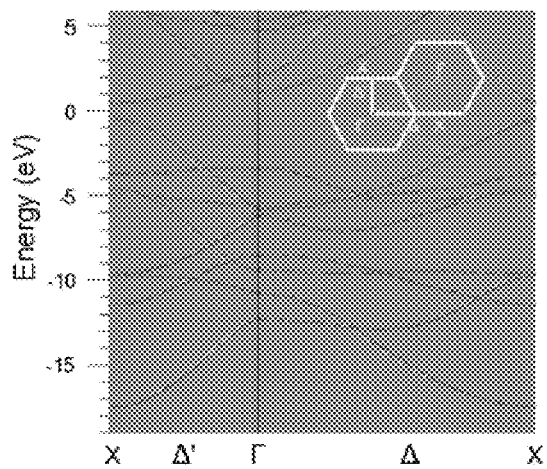
FIG. 7A is a graph plotting a calculated band structure for a GMO.
Figure 7B:
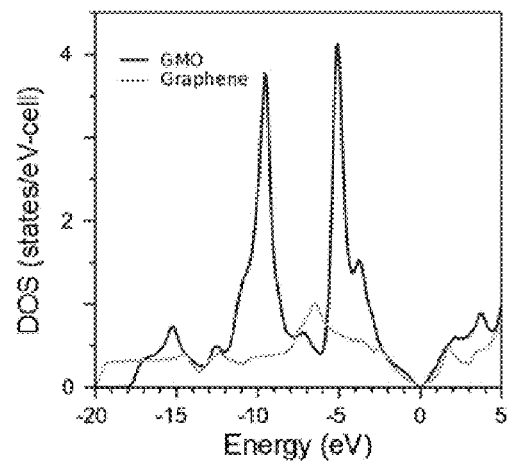
FIG. 7B is a graph plotting density of states for GMO and a graphene according to embodiments of the present invention.
Figure 12:
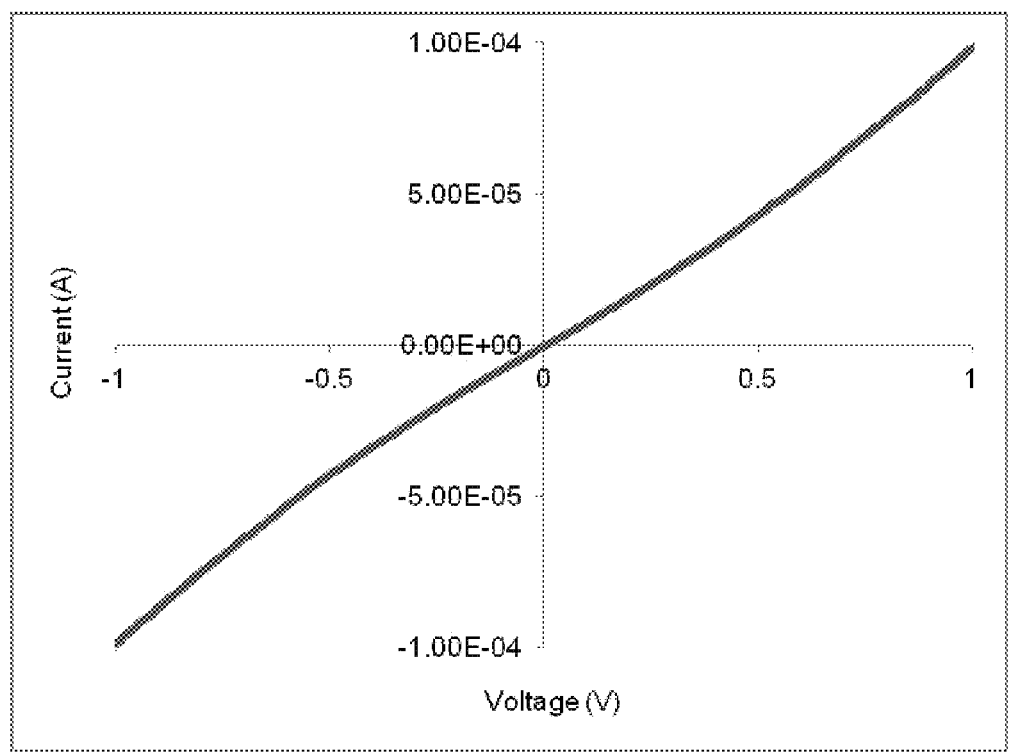
FIG. 12 is a current-voltage graph of a TRG-O according to an embodiment of the present invention.

Referring to FIG. 7, a direct band gap of approximately 0.9 eV is shown at the X point of a GMO according to an embodiment of the present invention. The size (and existence) of the gap was dependent on the distortion of the lattice away from the ideal hexagonal lattice: constraining GMO to be hexagonal (i.e., an angle of 120°) resulted in a zero gap semiconductor. The overall shapes and magnitudes of the density of states (DOS) of GMO and graphene within ±2 eV of the Fermi level (beyond the gap) were very similar. Transport measurements (FIG. 12) showed that the resistivity of as-reduced TRG-O is consistent with a GMO and graphene complex.

In summary, the vacuum thermal reduction of multilayer GO films yielded a composite material containing graphene and graphene monoxide nanocrystalline regions. The atomic structure of GMO, consistent with all experimental evidence from electron diffraction and IRMS, possessed an O:C=1:1 stoichiometry, with double-epoxide GMO units arranged on a 2D quasi-hexagonal lattice. Crystalline CO had never been observed in nature at standard temperature and pressure.

Example 2

Thermal Reduction of Graphene Oxide in Vacuum

Figure 13:
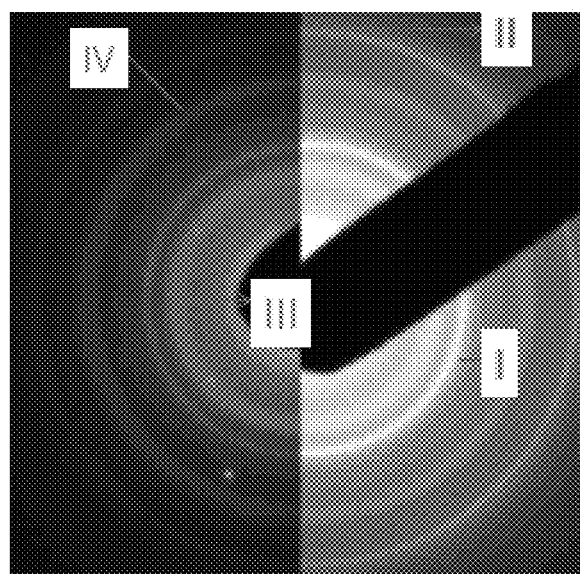
FIG. 13 is an SAED pattern of a GMO synthesized according to an embodiment of the present invention.
Figure 15A:
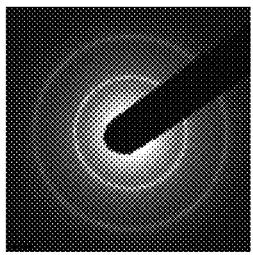
FIGS. 15A, 15B, 15C, and 15D are SAED patterns showing G rings (visible in all patterns) and GMO rings (visible in FIGS. 15C and 15D) according to an embodiment of the present invention (a) at 22° C., (b) at 555° C., (c) at 738° C., and (d) after cooling the sample to 28° C.
Figure 15B:
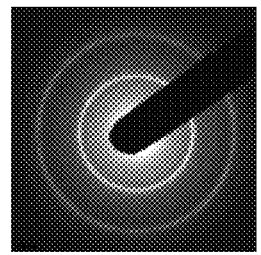
Figure 15C:
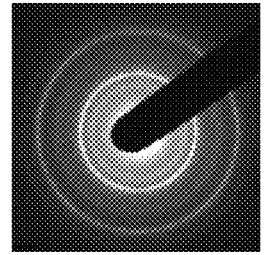
Figure 15D:
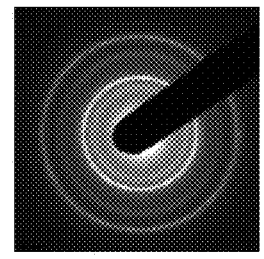

Graphene monoxide was synthesized by drop casting 1 µl of blue GO solution followed by 1 µl of GO solution (0.2 mg/ml, Austin sample) on a nickel TEM grid and dried in air for at least an hour. The specific blue GO solution was synthesized by immersing a Mo Transmission Electron Microscope (TEM) grid in 0.05 ml of GO (0.2 mg/ml, Austin sample) solution for 9 days. The resulting cast and grid were subjected to vacuum at approximately $1.3 \times 10^{-5}$ Pa and heated in-situ to high temperatures. Electron diffraction patterns were recorded from regions that were exposed to the electron beam during annealing, and also from regions that were not irradiated by electrons at the elevated temperatures. Referring to FIG. 13, alpha phase GMO was first observed at 550° C. Graphene was also observed along with molybdenum dioxide at 600° C., with and without electron beam irradiation.

Example 3

Thermal Reduction of Graphene Oxide in Vacuum

Graphene monoxide was synthesized by drop casting 1 µl of blue GO solution followed by 1 µl of GO solution (Austin sample) on a nickel TEM grid and dried in air for at least an hour. The specific blue GO solution was synthesized by immersing a Mo Transmission Electron Microscope (TEM) grid in 0.05 ml of ACS GO solution for 9 days. The resulting cast and grid were subjected to vacuum at approximately $1 \times 10^{-4}$ Pa in a bell jar and heated in a tantalum boat to a temperature exceeding 1200° C. Referring to FIG. 14, in addition to diffraction rings that are typical of GMO spacings, also called 2D alpha phase in our lab books, spots are also seen that correspond to spacings of the 3D beta phase consistent with $MoO_2$.

Example 4

Thermal Reduction of Graphene Oxide in Vacuum

Graphene monoxide was synthesized from GO solution. A molybdenum wire (3 cm long, 0.03" in diameter) was immersed in 1 ml of GO solution (1 mg/ml) for two months. The GO was prepared from natural graphite powder (Bay Carbon, SP-1 graphite) using the modified Hummers method with $H_2SO_4$, $KMnO_4$, $H_2O_2$, and HCl. The GO solution was prepared by dispersing the prepared GO powder into water with the help of ultrasonication (described in Nanoscale, 2011, 3, 2849, which is incorporated herein by reference). A 1 µl volume of the resulting GO solution (after adding the Molybdenum wire) was drop cast on a nickel wire grid and dried in air for at least an hour. Referring to FIG. 15, the resulting cast and grid were subjected to vacuum at approximately $1.3 \times 10^{-5}$ Pa and heated inside the TEM while monitored using SAED. Graphene monoxide diffraction rings become visible at the highest annealing temperature.

Example 5

Thermal Reduction of Graphene Oxide in Vacuum

Graphene monoxide was prepared by placing a new molybdenum TEM grid into 0.25 ml GO solution from ACS materials (0.5 mg/ml) for 10 days, drop casting 2 µl onto a nickel TEM grid and dried in air for at least an hour. The resulting cast and grid were subjected to vacuum at $1.3 \times 10^{-5}$ Pa and heated inside the TEM while monitored using SAED. The starting Mo grid was studied by XPS and found to have predominant surface oxidation composition of $MoO_2$, with smaller presence of $MoO_3$.

Figure 16A:
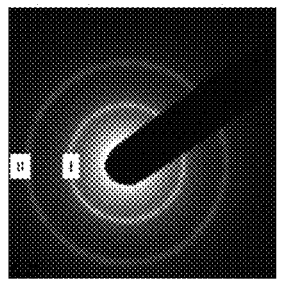
FIGS. 16A and 16B are SAED patterns of a GMO according to an embodiment of the present invention (a) at 23° C. and (b) at 750° C. after 31 minutes.
Figure 16B:
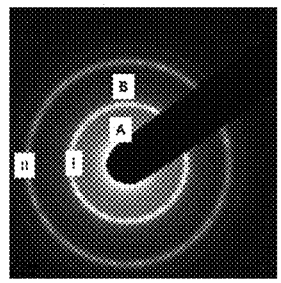

Referring to FIG. 16 (b), there was a hint of formation of rings Ring A (0.272 nm) and B (0.161 nm), which are equivalent to Ring III (0.260 nm) and Ring IV (0.152 nm), but expanded by 4.6% and 6.6% respectively.

Example 6

Thermal Reduction of Graphene Oxide in Vacuum

Graphene monoxide was prepared by placing new Molybdenum TEM grid into 0.25 ml GO solution (0.2 mg/ml, Austin sample) for 10 days, with 2 µl drop cast onto a nickel TEM grid and dried in air for at least an hour. The resulting cast and grid were subjected to vacuum at $1.3 \times 10^{-5}$ Pa and heated inside a TEM while monitored using SAED. This method yielded sample regions where graphene monoxide was present with relaxed interatomic spacings and other regions with spacings that were larger by a few percent.

Referring to FIG. 17 (c), graphene monoxide was not observed until a temperature of 757° C. after 35 minutes was reached but the signal of the graphene monoxide ring was faint. Referring also to FIG. 17 (e), an additional 10 minutes annealing showed stronger graphene monoxide rings (labeled III and IV), visible in many regions of the sample. Referring also to FIGS. 17(d) and (f), second region type was found where the rings (labeled A and B) have measurably smaller diameters indicative of a structure was still quasi-hexagonal but with larger unit cell than the typical graphene monoxide structure by a few percent. This expanded lattice was seen both after 45 and 55 minutes of annealing time and it coexisted with the relaxed lattice in space and annealing time.

Example 7

Thermal Reduction of Graphene Oxide in Vacuum

Figure 18A:
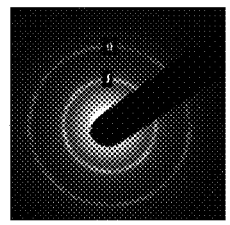
FIGS. 18A, 18B, and 18C are SAED patterns of a GMO according to an embodiment of the present invention (a) of a first region at 22° C., (b) of the first region at 759° C., and (c) of a second region at 759° C. close to a molybdenum trioxide particle.
Figure 18B:
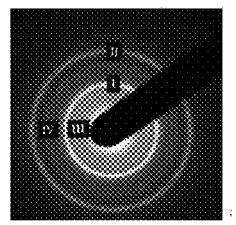
Figure 18C:
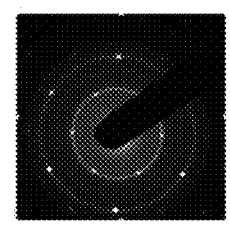

Graphene monoxide was synthesized from a blue GO solution drop cast onto a nickel TEM grid and dried in air. The specific blue GO solution was synthesized by immersing 50 mg of Mo powder in 0.5 ml of GO solution (from Advanced Chemical Suppliers Material, referred to as "ACS GO solution"), for 15 minutes. The resulting cast and grid were subjected to vacuum at $1.3 \times 10^{-5}$ Pa and heated inside a TEM while monitored using SAED. Molybdenum trioxide microparticles were observed in some sample regions before heating. Referring to FIG. 18, standard grapene monoxide is produced in most specimen regions except close to the original molybdenum-rich microparticles where additional diffraction spots appeared in SAED.

Example 8

Thermal Reduction of Graphene Oxide in Vacuum

Figure 19A:
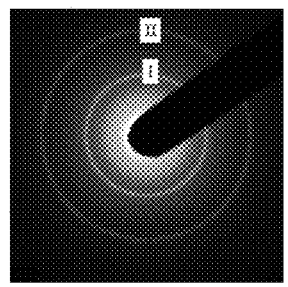
FIGS. 19A and 19B are SAED patterns of a GMO according to an embodiment of the present invention (a) of a second region at 22° C. and (b) of the second region at 755° C.
Figure 19B:
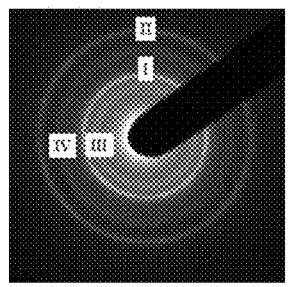

Graphene monoxide was synthesized from a blue GO solution drop cast onto a nickel TEM grid and dried in air. The specific blue GO solution was synthesized by immersing 50 mg of Mo powder in 0.5 ml of ACS GO solution for 30 minutes. The resulting cast and grid were subjected to vacuum at $1.3 \times 10^{-5}$ Pa and heated inside a TEM while monitored using SAED. Particles of approximately 1 micron were found before heating in some sample regions. Referring to FIG. 19, the graphene monoxide rings were formed, albeit some diffraction spots evolved and disappeared during heating. At 750° C., a couple of diffraction spots appeared due to Ni{100}.

Example 9

Thermal Reduction of Graphene Oxide in Vacuum

Figure 20A:
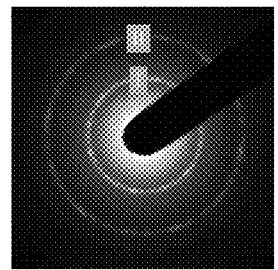
FIGS. 20A and 20B are SAED patterns of a GMO according to an embodiment of the present invention (a) of a first region at 22° C. and (b) of the first region at 753° C.
Figure 20B:
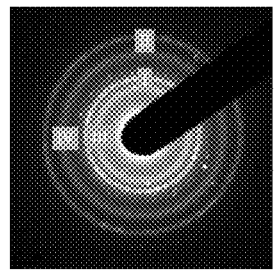

Graphene monoxide was synthesized from a blue GO solution drop cast onto a nickel TEM grid and dried in air. The specific blue GO solution was synthesized by immersing 50 mg of Mo powder in 0.5 ml of ACS GO solution for 60 minutes. The resulting cast and grid were subjected to vacuum at approximately $1.3 \times 10^{-5}$ Pa and heated inside a TEM while monitored using SAED. Referring to FIG. 20, in addition to the formation of graphene monoxide rings, spotty diffraction rings also form which are consistent nanoparticles of $MoO_2$. The spotty rings of molybdenum dioxide nanoparticles were found by the inventors in their earlies experiments and called beta phase, when the smooth rings of graphene monoxide were labeled as alpha phase.

Example 10

Synthesis with Addition of Water Vapor in Vacuum

A starting GMO/G sample was synthesized by drop casting 2 μl of graphene oxide (0.2 mg/ml; Austin material) in a distilled water dispersion solution onto a bare 200 mesh molybdenum transmission electron microscope grid and subsequent vacuum annealing of the air dried sample. The GO cast on the Mo grid was subjected to vacuum of approximately $1.3 \times 10^{-5}$ Pa while heating the cast GO and grid to 800° C. at a rate of 30° C./min. The formation of graphene monoxide rings was detected through electron diffraction with 300 keV electrons. The sample was cooled to room temperature, removed from the vacuum, and transported through air from Wisconsin to Arizona for additional in-situ thermal annealing under varying pressure of water vapor.

Selected area electron diffraction (SAED) was recorded as function of temperature and $H_2O$ partial pressure in a specialized Environmental Transmission Electron Microscope (ETEM) designed to allow introduction of water vapor in the vacuum of the microscope while probing with 200 keV electrons. The sample was also studied with electron energy loss spectroscopy (EELS), with special emphasis on temperature/pressure conditions when changes were seen in the GMO diffraction rings. Notably, the alpha-phase and the graphene diffraction rings remained constant upon annealing in $1.3 \times 10^{-5}$ Pa vacuum at approximately 200° C. for approximately 1 day; and also after adding water vapor with partial pressures up to approximately 133 Pa at the same low temperature. Further heating in $H_2O$ partial pressure of approximately 13 Pa resulted in formation of additional GMO material after the temperature increased beyond approximately 500° C. This was demonstrated by ongoing increases in the intensity in the alpha-phase diffraction rings, indicating increased area of the ordered two-dimensional crystalline structure (i.e. GMO). The graphene (G) rings did not disappear under the conditions used, indicating that the material continued to contain both 2D lattices (G and GMO), but with increased GMO to G area ratio. Diffraction rings consistent with 3D nano-crystallites of $MoO_2$ (i.e. the beta phase) started to form at approximately 750° C. The fact that the alpha and beta phases are formed under irradiation with 300 keV and 200 keV electrons indicates that the energy of the electron irradiation may not be critical for their formation, and that the graphene monoxide structure may remain stable under such irradiation.

Example 11

Synthesis with Addition of Water Vapor in Vacuum

Graphene monoxide was synthesized by drop casting 2 μl of graphene oxide (0.2 mg/ml; Austin material) in a distilled water dispersion solution onto a bare 200 mesh Molybdenum transmission electron microscope grid and dried in air. The GO cast on the Mo grid was subjected to a base vacuum of approximately $1.3 \times 10^{-5}$ Pa, then exposed to water vapor with partial pressure of approximately 133 Pa for approximately 1 hr at approximately 500° C., without exposure to the 200 keV electron beam. The diffraction rings associated with the alpha phase (GMO) were observed and were shown to be enhanced in intensity by exposure to water. Additional pressures of 13-1,330 Pa were explored. Both temperature and water partial-pressure were found to be important for the ease of formation of the alpha rings.

Example 12

Figure 21A:
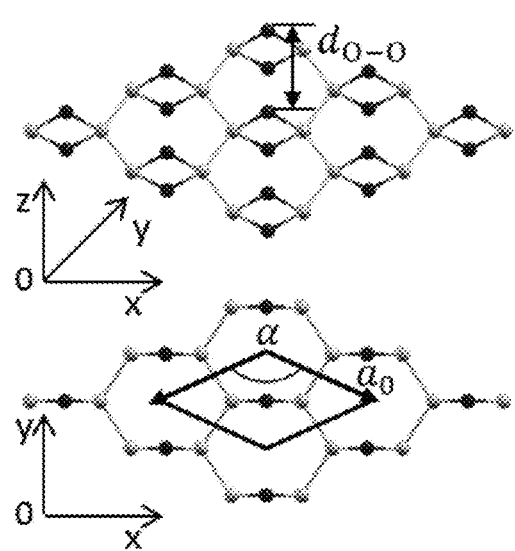
FIGS. 21A and 21B are schematic illustrations of a GMO according to an embodiment of the present invention.

Strain-Induced Band Gap Engineering of Graphene Monoxide and its Effect on Graphene To explore the interplay between the mechanical and electronic properties of pure GMO and its one-dimensional interface with graphene, first-principles calculations were done using the Full-potential Linearized Augmented Plane Wave (FLAPW) method as implemented in flair. A plane wave cutoff of 275 eV was used for the expansion of the wave functions, the Brillouin zone was sampled using a 12×12×1 mesh, and the generalized gradient approximation (GGA) for exchange-correlation was used. FIG. 21(a) shows the crystalline structure of GMO. Each C atom forms four bonds, two along the zigzag direction to the neighboring C atoms, and two with the bridging O atoms along the armchair direction. The two-dimensional centered-rectangular (quasi-hexagonal) structure can be described by two of three interrelated parameters: the length of the rhombus edge, $a_o$, the opening angle α (equal to 120° for hexagonal systems), and the width of the conventional rectangular cell [$d_{O-O}$ in FIG. 21(a)]. The internal atomic positions of all the atoms were fully relaxed ($3\times10^{-3}$ eV/A) for each set of parameters.

Figure 21B:
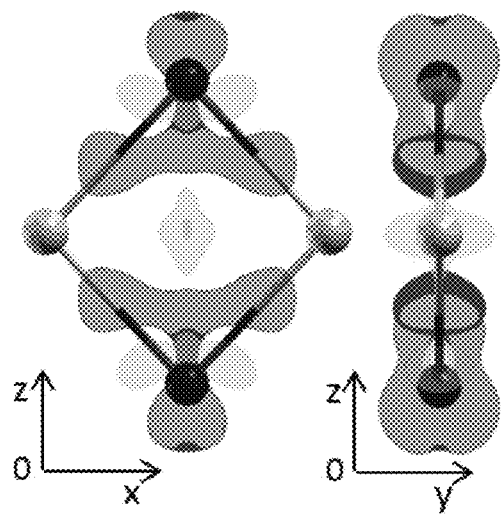
Figure 23A:
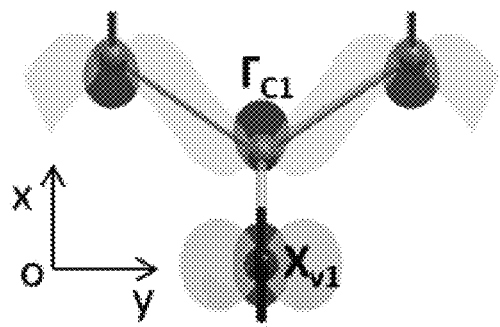
FIGS. 23A, 23B, 23C, and 23D are schematic illustrations of charge distributions of states for GMOs according to embodiments of the present invention.
Figure 23B:
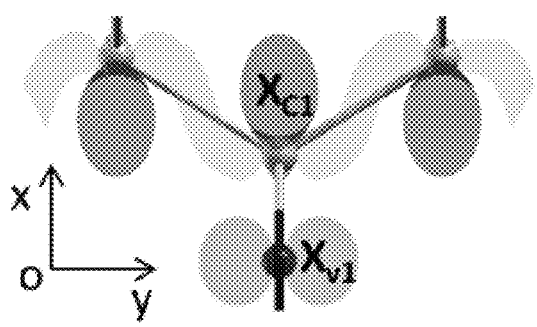
Figure 23C:
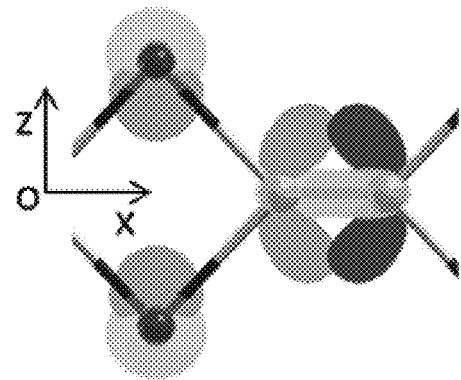
Figure 23D:
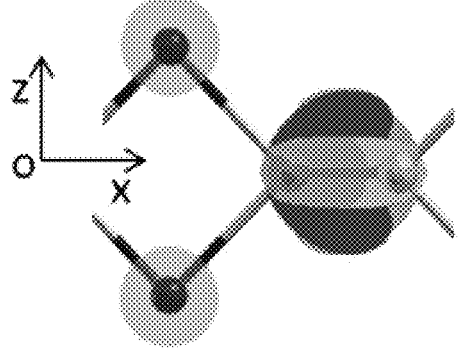

For the fully relaxed ground state structure (a0=3.10 Å, α=130°), the C—C bond length (1.56 Å) was close to typical values (approximately 1.54 Å) of C $sp^3$ bonds, while the C—O bond length (1.43 Å) was comparable to $sp^2$ C—C bonds (1.42 Å). Though not wishing to be bound by a particular theory, since the stiffness of graphene is strongly dependent on the planar $sp^2$ σ bonds, the large C—C bond lengths compared with graphene suggested (and borne out by the calculations) that GMO is less rigid than graphene. The higher electronegativity of O (3.44) than that of C (2.55) was consistent with the calculated result [cf., FIG. 21(b)] that electrons accumulated near the C—O bonds and the O atoms.

The calculated trends in the distortion energies of GMO as a function of α and dO-O are given in FIG. 22(a). The energy cost for rather large distortions was small, and the "energy valley" was approximately aligned along constant $a_o$ (=3.10 Å). External strains were accommodated mainly by changes in a (or equivalently, $d_{O-O}$) rather than by changes in $a_o$: The low-energy structure has a modulus of approximately 570 GPa along the zigzag direction, about half of the graphene modulus (approximately 1.1 TPa). FIG. 22(b) presents the calculated band gaps corresponding to the structure parameters in FIG. 22(a). For the fully optimized structure, GMO is a semiconductor with a calculated indirect band gap of approximately 0.6 eV. Upon planar deformation, GMO spans the range of semiconducting (both indirect- and direct-gap) and metallic behaviors. Stretching along the zigzag direction (increasing $d_{O-O}$), caused the band gap of GMO to vary from approximately 0.6 eV (indirect-gap, at 130°) up to approximately 1.4 eV (both indirect- and direct-gap, at 126°), then down to approximately 0.1 eV (direct-gap, at 121°). The sensitive response of the band gap to external strains in GMO may be attractive for low-cost fabrication of building blocks in nanoelectromechanical systems (NEMS). In contrast, depending on the use requirement or other preferences for the particular NEMS, graphene may not be an ideal candidate for NEMS, since the electronic structure of graphene is robust against external strains up to approximately 23% while the fracture strain is approximately 25%. Moreover, although the band gap of GNR with armchair edges has been theoretically predicted to be tunable by mechanical perturbations and may have a semiconductor-metal transition as the strain increases, the uniaxial modulus of these GNRs is extremely large, approximately 7 TPa, and therefore may not be suitable for practical NEMS applications Referring to FIGS. 22(c) and 22(d), representative band structures are shown for the same $a_o$, but different angles α. The low-lying conduction bands exhibited large variations, while the valence bands had small changes, as a varies from 130° to 125°: The conduction band state labeled $\Gamma_{C1}$ ($\Gamma_{C1}$) undergoes an upward (downward) shift of approximately 0.8 eV (2.6 eV), while $X_{V1}$ moves down approximately 0.1 eV. Such band shifts were indicative of significant changes in the interactions between atomic orbitals on different sites with respect to angle α for a fixed lattice constant $a_o$. FIGS. 23(a)-(d) present the charge density distributions corresponding to the states at the top and the bottom of the gap, as labeled in FIGS. 22(c) and 22(d). The conduction band edge states ($\Gamma_{C1}$ and $X_{C1}$) exhibited different character, with $X_{C1}$ having no O 2p contributions. On the C atoms, the conduction states were predominantly $p_z$ for $\Gamma_{C1}$ (IGMO), whereas for $X_{C1}$ (DGMO) there was a strong admixture of $p_x$. Though not wishing to be bound by a particular theory, since the C $p_x$-$p_x$ interaction varies as $l^2 V_{pp\sigma}+(1-l^2) V_{pp\pi}$, where l is the direction cosine and $V_{pp\sigma}$, $V_{pp\pi}$ are Koster-Slater tight-binding parameters, the energy of the $X_{C1}$ state in particular changed significantly with α, as seen in FIGS. 22(c) and 22(d). The gap edge valence state $X_{v1}$, on the other hand, was predominantly O $p_y$ (with small admixture of $p_z$) and bonding C $sp^2$ ($p_x$, $p_y$) orbitals that would form a conduction network along the zigzag direction for p-doped GMO.

Figure 24:
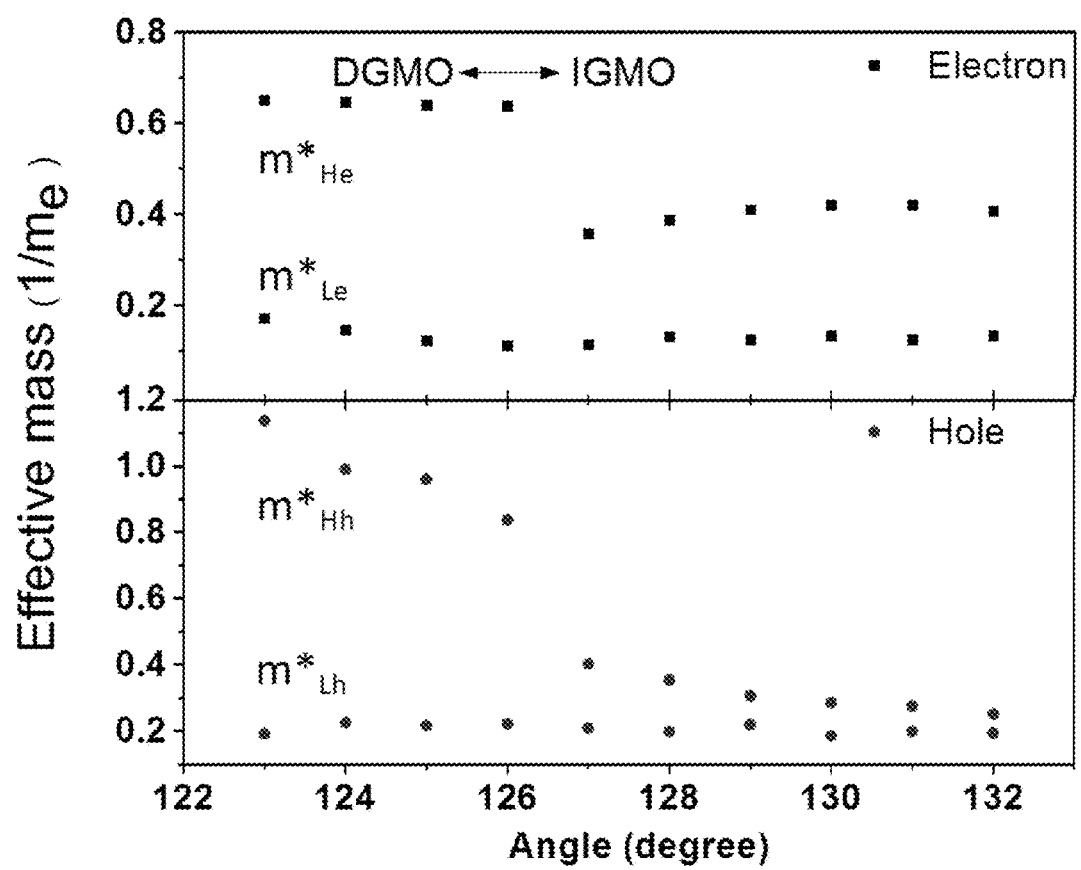
FIG. 24 is a graph plotting effective mass of carriers in a GMO according to an embodiment of the present invention.

The band gap (width and type) and the charge carrier mobility—which is inversely proportional to its effective mass—can be important features for semiconductor-based device applications. As shown above, GMO may be either a direct or indirect band gap semiconductor, and has a tunable band gap. As a measure of the transport properties, FIG. 24 shows the effective masses for electrons and holes as a function of the angle α. The electron effective masses changed dramatically when GMO switched from indirect- to direct-gap semiconductor as a result of the conduction band minimum changing from Γ to X. The hole mass along the armchair direction (X to F) remained fairly constant, but there was an increase along the zigzag direction with decreasing a. In the case of IGMO, the light electrons (preferred conduction) were along the armchair or longitudinal direction, i.e., through the C—O—C double epoxy units; in the case of DGMO, the light electrons were in the zigzag direction through the . . . —C—C—C— . . . network. For the holes, the preferred conduction was along the armchair direction for both IGMO and DGMO. The calculated GMO effective masses ($m^*_{Le}/m_e$=0.112-0.132, $m^*_{Lh}/m_e$=0.185-0.225) were larger than those in Ge ($m^*_{Le}/m_e$=0.041, $m^*_{Lh}/m_e$=0.044) and group III-V semiconductors ($m^*_{Le}/m_e$=0.015-0.11, $m^*_{Lh}/m_e$=0.021-0.082), but they were comparable to those of Si ($m^*_{Le}/m_e$=0.20, $m^*_{Lh}/m_e$=0.15) and GNR with similar band gaps ($m^*_{Le}/m_e$=$m^*_{Lh}/m_e$=0.075-0.10 for band gaps of 0.2-0.5 eV, with the effective mass drastically increasing above 0.1 when the band gap exceeds 0.5 eV).

To investigate how the interface between a graphene matrix and GMO affects the electronic structure of both graphene and GMO, a simplified model of the combined system consisting of a periodic array of approximately 30 Å stripes of both graphene and GMO was considered, with the interface along the zigzag direction and with $d_{O-O}$ of GMO fixed to the corresponding distance in graphene [FIG. 25(a)], thus the atoms in the GMO region were relaxed only along the armchair direction; at this $d_{O-O}$ GMO was metallic [cf., FIG. 22(b)]. Energetically there was a cost related to this distortion of the GMO, but the formation of GMO was still energetically more favorable (by approximately 0.2 eV/O-atom in the calculations) than forming isolated epoxide groups or carbonyl pairs, which are among the most stable functional groups in graphene oxide.

FIG. 25(b) shows the (local) band structure of the combined system in the middle of the graphene region and k-projected ("unfolded") onto the graphene 1×1 Brillouin zone. In contrast to graphene, there was a band gap of approximately 0.5 eV at the K' point—Γ-K'-M corresponding to propagation along the graphene ribbon—with almost linear dispersion, as shown in the inset. (The bands at the nominally equivalent K' and K points for pristine graphene were different here.) This induced gap was significantly larger than the gap of approximately 0.2 eV expected for zigzag GNRs of the same width, pointing out the influence of the graphene-GMO interface. FIG. 25(c) shows the local k-projected band structure of the GMO region. The electronic states from graphene extend throughout the approximately 30 Å wide GMO region: Although in pure GMO (cf., FIG. 22), there are no states within several eV of the Fermi level at K', images of the graphene bands in FIG. 25(b) were clearly seen along Γ-K'-X' in FIG. 25(c). The gap at K' in the graphene region had increased (doubled) to approximately 1 eV in the GMO region of the composite. (The bands around K' displayed aspects of being at a high symmetry point, which is true for pure graphene, but not GMO, further evidence of the leakage of graphene states.) Similarly, there were remnants of the GMO bands in the graphene region, i.e., there was a complicated superimposition and entanglement of graphene and GMO states near the interface. The effects of the lateral confinement and interaction effects due to the finite widths of the ribbons were particularly noticeable along X-Γ (and M-Γ of the graphene) since this is the direction corresponding to propagation across the interface. In the GMO region, there were two sets of bands that form a staircase of states with fairly well-defined momenta and energies. These bands corresponded to those shown in FIGS. 23(a) and 23(c); the other bands did not show the same staircase behavior, indicating that the origin of the staircases was not simply confinement to the GMO ribbon. These GMO states, in fact, extended into the graphene, being the dominant states along M-Γ within a few eV of the Fermi level, FIG. 25(b).

To further explore the tunable electronic properties of GMO by small external mechanical strain, the effect of uniform compressive strain along the armchair direction of GMO was investigated, assuming that the hexagonal symmetry of graphene was maintained due to the large difference of Young's moduli. For a compressive strain of approximately −2.5%, GMO was still metallic and the band structure of graphene maintained the same features, except the graphene band gap decreased to approximately 0.4 eV. If the strain was increased to −3.5%, however, the band gap of graphene increased to approximately 0.6 eV and GMO became semiconducting; therefore, GMO might also be used as a tool to tune the band gap in graphene at the G-GMO interface. These types of strains could potentially be realized in GMO—piezoelectric/ferroelectric nanostructure devices, allowing the active real-time modification of the band gap.

In sum, the band gap of GMO was found to be sensitive to the lattice angle (120°-134°) and vary between 0 to over 1.3 eV, with the nature of the band gap switching from direct to indirect as the lattice angle increases. Electron and hole transport occurred predominantly along the zigzag and armchair directions (armchair for both) when GMO is a direct- (indirect-) gap semiconductor. A band gap of approximately 0.5 eV was also induced in graphene at the K' points for GMO/graphene hybrid systems.

Thus, the present invention provides graphene-based nanomaterials generally including at least one atomic layer of graphene monoxide and methods of synthesizing the graphene-based nanomaterials. Various alternatives are contemplated as being within the scope of the following claims, particularly pointing out and distinctly claiming the subject matter regarded as the invention.

What is claimed is:

1. A composition of graphene-based nanomaterials, the composition comprising: at least one atomic layer of graphene monoxide, wherein the grapheme monoxide is crystallographically ordered at least in part and configured to form a plurality of diffraction rings when probed by an incident electron beam; and
a nanocrystalline oxide or carbide, wherein the nanocrystalline oxide is a transition metal oxide and wherein the nanocrystalline carbide is a transition metal carbide.

2. The composition of claim 1, further comprising at least one atomic layer of graphene.

3. The composition of claim 1, wherein the nanocrystalline oxide is molybdenum oxide.

4. A nanostructure comprising graphene-based nanomaterials according to claim 1, wherein the nanostructure is configured to support at least one of a metal or metal oxide atom, cluster, and nanocrystal.

5. A gas sensor comprising:
(a) one or more electrodes formed on a substrate and adapted to be operatively connected to a meter to measure an electrical characteristic between the electrodes;
(b) one or more nanostructures in contact with the one or more electrodes; and
(c) one or more nanoparticles deposited on the nanostructures, wherein the nanoparticles include the graphene-based nanomaterials according to claim 1.

6. An electrochemical cell comprising:
an anode including the graphene-based nanomaterials according to claim 1;
a cathode;
a separator; and
an electrolyte.

7. An electronic device comprising:
one or more semiconducting elements including the graphene-based nanomaterials according to claim 1; and
one or more junctions positioned between the graphene-based nanomaterials, the junctions including conducting and insulating materials, wherein the graphene-based nanomaterials are associated with a tunable energy bandgap.

* * * * *